United States Patent
Banerjee

(10) Patent No.: US 11,567,096 B2
(45) Date of Patent: Jan. 31, 2023

(54) SENSING FOR AUTOMATED BIOLOGICAL CELL INJECTION

(71) Applicant: Mekonos Limited, Auckland (NZ)

(72) Inventor: Arunava Steven Banerjee, San Francisco, CA (US)

(73) Assignee: Mekonos Limited, Auckland (NZ)

( * ) Notice: Subject to any disclaimer, the term of this patent is extended or adjusted under 35 U.S.C. 154(b) by 568 days.

(21) Appl. No.: 16/346,526

(22) PCT Filed: Oct. 31, 2017

(86) PCT No.: PCT/NZ2017/050141
§ 371 (c)(1),
(2) Date: Apr. 30, 2019

(87) PCT Pub. No.: WO2018/080325
PCT Pub. Date: May 3, 2018

(65) Prior Publication Data
US 2020/0150141 A1     May 14, 2020

(30) Foreign Application Priority Data

Oct. 31, 2016    (AU) ................................. 2016904438

(51) Int. Cl.
*G01N 35/10* (2006.01)
*B25J 7/00* (2006.01)
(Continued)

(52) U.S. Cl.
CPC ................ *G01N 35/10* (2013.01); *B25J 7/00* (2013.01); *G01N 35/00584* (2013.01);
(Continued)

(58) Field of Classification Search
CPC .. G01N 35/10; G01N 35/00584; G01N 23/00; B25J 7/00; C12M 1/12;
(Continued)

(56) References Cited

U.S. PATENT DOCUMENTS

| 5,262,128 A | 11/1993 | Leighton et al. |
| 6,264,815 B1 * | 7/2001 | Pethig ............... B03C 5/005 204/547 |

(Continued)

FOREIGN PATENT DOCUMENTS

| CN | 105441325 A | 3/2016 |
| WO | 2008034249 A1 | 3/2008 |

(Continued)

OTHER PUBLICATIONS

Search Report and Written Opinion from related Singapore Patent Application No. 11201903750R, dated Jun. 23, 2020, 14 pages.

(Continued)

*Primary Examiner* — Benjamin R Whatley
*Assistant Examiner* — Curtis A Thompson
(74) *Attorney, Agent, or Firm* — Norton Rose Fulbright US LLP

(57) ABSTRACT

A method of controlling a needle actuator to interact with a cell is provided, the method comprising: providing an actuator comprising a tower, a stage and a needle, wherein the needle is mounted on the stage; applying an electrostatic potential between the tower and the stage to retract the needle; moving the actuator towards the cell; reducing the potential so as to allow the stage and needle to move towards the cell; applying calibration data to detect when the needle has pierced the cell; and reducing the potential further once it has been detected that the needle has pierced the cell. The cell can be a biological cell. The needle can be a micro-needle and the stage can be a micro-stage.

23 Claims, 9 Drawing Sheets

(51) Int. Cl.
*G01N 35/00* (2006.01)
*H01L 23/58* (2006.01)
*G21K 7/00* (2006.01)
*G01N 23/00* (2006.01)
*H01L 21/302* (2006.01)
*C12N 13/00* (2006.01)
*C12M 1/00* (2006.01)
*C12M 1/12* (2006.01)
*C12M 1/32* (2006.01)

(52) U.S. Cl.
CPC ............... *C12M 1/00* (2013.01); *C12M 1/12* (2013.01); *C12M 1/32* (2013.01); *C12N 13/00* (2013.01); *G01N 23/00* (2013.01); *G21K 7/00* (2013.01); *H01L 21/302* (2013.01); *H01L 23/58* (2013.01)

(58) Field of Classification Search
CPC .......... C12M 1/32; C12M 1/00; C12M 35/00; C12M 23/12; C12M 23/50; C12M 33/06; H01L 23/58; H01L 21/302; G21K 7/00; C12N 13/00; B81B 2201/033; B81B 2201/055; B81B 3/0062; B01L 3/502761
See application file for complete search history.

(56) References Cited

U.S. PATENT DOCUMENTS

| | | | | |
|---|---|---|---|---|
| 6,645,757 | B1* | 11/2003 | Okandan | C12M 35/02 204/164 |
| 2003/0015807 | A1 | 1/2003 | Montemagno et al. | |
| 2007/0087436 | A1* | 4/2007 | Miyawaki | C12M 35/00 977/902 |
| 2007/0019422 | A1 | 8/2007 | Zorn | |
| 2007/0194225 | A1* | 8/2007 | Zorn | G01Q 10/06 250/306 |
| 2007/0220882 | A1* | 9/2007 | Culpepper | B81B 3/0062 60/527 |
| 2009/0291502 | A1* | 11/2009 | Tateyama | C12M 35/00 435/455 |
| 2011/0262891 | A1 | 10/2011 | Ozaki et al. | |
| 2012/0225435 | A1 | 9/2012 | Seger et al. | |
| 2013/0023052 | A1* | 1/2013 | Tanaka | G02B 21/32 435/461 |
| 2013/0077945 | A1 | 3/2013 | Liu et al. | |
| 2014/0323837 | A1 | 10/2014 | Hirshberg | |
| 2016/0252546 | A1* | 9/2016 | Amponsah | G01Q 70/10 850/55 |

FOREIGN PATENT DOCUMENTS

| | | |
|---|---|---|
| WO | 2013126556 A1 | 8/2013 |
| WO | 2014090415 A1 | 6/2014 |
| WO | WO-2014090415 A1 * | 6/2014 ............ C12M 23/04 |

OTHER PUBLICATIONS

AU/RO—Preliminary Report on Patentability of related International Application No. PCT/NZ2017/050141 dated May 9, 2019, 12 pgs.

AU/RO—Republication (A9) of related International Application No. PCT/NZ2017/050140 dated Apr. 18, 2019, 87 pgs.

AU/RO—International Preliminary Report on Patentability of related International Application No. PCT/NZ2017/050140 dated May 9, 2019, 8 pgs.

AU/RO—International Search Report of related International Application No. PCT/NZ2017/050140 dated Feb. 19 Jul. 2018, 11 pgs.

AU/RO—International Search Report of related International Application No. PCT/NZ2017/050141 dated Mar. 14, 2018, 17 pgs.

European Search Report dated Jun. 3, 2020 issued in co-pending European Patent App. No. 17864076.9 (6 pages).

* cited by examiner

SENSING FOR AUTOMATED BIOLOGICAL CELL INJECTION

CROSSED-REFERENCE OF RELATED APPLICATIONS

This is the national stage application filed under 35 U.S.C. § 371 of International Application PCT/NZ2017/050141, filed Oct. 31, 2017, which designated the United States of America, the disclosure of which is incorporated herein by reference, which claims the benefit Australian Application No. 2016904438, filed Oct. 31, 2016, the entire contents of which are hereby incorporated by reference.

FIELD

This disclosure relates to improvements with respect to sensing for automation of biological cell injection, such as, for example, injection of cells with needles carrying pharmacological, biological or chemical agents. The disclosure further relates to sensing for and automation of injection of biological cells using micro-scale or nanoscale robotic devices. The disclosure further relates to sensing for and automation of injection of biological cells using a parallel array of robotic devices.

BACKGROUND

Injecting biological cells can be achieved by using a microneedle or nanoneedle to penetrate the cell to deliver an agent to be injected. Conventional approaches involve using a device to move the needle in 3-D. Conventional devices use micro-engineered machine (MEMS) technologies involving devices formed from silicon wafer.

There is an accepted need to make biological cell injection operation as cost-effective as possible, and to provide an array of needle manipulators which results in improved throughput of biological cell injection operations and is readily controllable.

The applicant has observed potential advantage in injection operations involving a number of devices in parallel on a single silicon wafer.

The applicant has also observed a potential advantage in controlling a number of devices in parallel on a single silicon wafer.

SUMMARY

In an embodiment, a method of controlling a needle actuator to interact with a cell is provided, the method comprising: providing an actuator comprising a tower, a stage and a needle, wherein the needle is mounted on the stage; applying an electrostatic potential between the tower and the stage to retract the needle; moving the actuator towards the cell; reducing the potential so as to allow the stage and needle to move towards the cell; applying calibration data to detect when the needle has pierced the cell; and reducing the potential further once it has been detected that the needle has pierced the cell. The cell can be a biological cell. The needle can be a micro-needle and the stage can be a micro-stage.

Alternatively, the cell is held by a cell trap. The cell trap can comprise a plurality of microchambers, each microchamber arranged to hold a cell.

Alternatively, the method further comprises applying an electrostatic potential between the tower and the stage to retract the needle towards the stage.

Alternatively, the method further comprises reducing the potential to allow the stage and needle to move towards the cell while monitoring the potential and displacement of the stage to detect a fluctuation in voltage versus displacement to indicate that the needle has pierced the cell. Alternatively, a laser interferometer is used to indicate that the needle has pierced the cell.

Alternatively, the calibration data comprises data defining voltages for displacements stored against types of cells.

Alternatively, the actuator is provided on an array of actuators, each interacting with an individual cell of a plurality of cells.

In another embodiment, a method of generating calibration data for target voltage potentials associated with cell-type data is provided, the method comprising: providing a calibration apparatus comprising a manipulator and a cell trap, the manipulator comprising a tower, a stage, and a needle, wherein the needle is mounted on the stage; identifying a cell type to be calibrated; applying a voltage so as to pull the stage towards the tower in a retracted position; moving the manipulator to within a defined range of the cell-trap configured to house a cell type; changing the voltage to allow the stage and mounted needle to be forced away from the tower and the retracted position while measuring the displacement of the stage; determining when the needle has reached a target region; and recording actuation data for use in cell injection for the identified cell type.

Alternatively, the method further comprises receiving a user input of the cell type to a controller provided on the calibration apparatus.

Alternatively, the method further comprises applying a voltage to an actuator provided on the calibration apparatus, so as to pull the stage towards the tower in a retracted position.

Alternatively, the method further comprises moving the manipulator to within the defined range of the cell-trap, wherein a camera provided on the calibration apparatus is programmed to determine if the manipulator is within the defined range. The camera on the calibration apparatus can alternatively be programmed to determine if the manipulator is within the defined range of a periphery of the cell trap.

Alternatively, the method further comprises reducing the voltage to allow the stage and mounted needle to be forced away from the tower and the retracted position while measuring the displacement of the stage. Measuring the displacement of the stage can be performed by a laser interferometer provided in the calibration apparatus.

Alternatively, the actuation data is selected from a group consisting of a record target voltage, a target vertical actuation displacement, a point of penetration, a point of poking, a Voltage-Displacement characteristic curve distortion, and combinations thereof.

In another embodiment, a non-transitory computer-readable medium in which a program is stored for causing a computer to perform a method for generating calibration data for target voltage potentials associated with cell-type data is provided, the method comprising: providing a calibration apparatus comprising a manipulator and a cell trap, the manipulator comprising a tower, a stage, and a needle, wherein the needle is mounted on the stage; identifying a cell type to be calibrated; applying a voltage so as to pull the stage towards the tower in a retracted position; moving the manipulator to within a defined range of the cell-trap configured to house a cell type; changing the voltage to allow the stage and mounted needle to be forced away from the tower and the retracted position while measuring the displacement of the stage; determining when the needle has reached a target region; and recording actuation data for use in cell injection for the identified cell type.

Alternatively, the method further comprises receiving a user input of the cell type to a controller provided on the calibration apparatus.

Alternatively, the method further comprises applying a voltage to an actuator provided on the calibration apparatus, so as to pull the stage towards the tower in a retracted position.

Alternatively, the method further comprises moving the manipulator to within the defined range of the cell-trap, wherein a camera provided on the calibration apparatus is programmed to determine if the manipulator is within the defined range. The camera on the calibration apparatus can be alternatively programmed to determine if the manipulator is within the defined range of a periphery of the cell trap.

Alternatively, the method further comprises reducing the voltage to allow the stage and mounted needle to be forced away from the tower and the retracted position while measuring the displacement of the stage. The measuring the displacement of the stage can be performed by a laser interferometer provided in the calibration apparatus.

Alternatively, the actuation data is selected from a group consisting of a record target voltage, a target vertical actuation displacement, a point of penetration, a point of poking, a Voltage-Displacement characteristic curve distortion, and combinations thereof.

In yet another embodiment, a system for controlling a needle actuation to interact with a cell is provided, the system comprising: an injection device comprising a tower, stage, needle and actuator, the needle mounted on the stage, and the actuator arranged and configured to apply a voltage potential to the stage to move the needle toward and away from the tower; a cell trap configured to house a cell to be penetrated by the needle of the injection device; a first camera configured and arranged to monitor a proximity of the injection device to the cell trap; and a controller configured to control the movement of the injection device. The first camera can be configured and arranged to monitor movement on a Z-axis.

Alternatively, the injection device further comprises a plurality of actuators.

Alternatively, the system further comprises a second camera configured and arranged to monitor the alignment between the injection device and the cell trap. Alternatively, the first camera is configured and arranged to monitor movement on a Z-axis, and wherein the second camera is configured and arranged to monitor movement on the X-axis and Y-axis.

Alternatively, the system further comprises a microscope comprising a second camera, the microscope configured and arranged to monitor the alignment between the injection device and the cell trap. Alternatively, the first camera is configured and arranged to monitor movement on a Z-axis, and wherein the microscope is configured and arranged to monitor movement on the X-axis and Y-axis. The microscope can be an inverted microscope.

Alternatively, the system further comprising a macro-stage configured and arranged to control movement of the injection device.

In a further embodiment, a method for controlling a cell injection device is provided, the method comprising: providing an apparatus comprising a cell injection device, a cell trap, and a storage device, the cell injection device comprising a tower, a stage, and a needle, wherein the needle is mounted on the stage; identifying a cell type to be injected; retrieving actuation data from the storage device; applying a voltage so as to pull the stage towards the tower in a retracted position; moving the cell injection device to within a defined range of the cell-trap configured to house a cell type; applying a varying target actuation voltage based on retrieved actuation data to allow the stage and mounted needle to be forced away from the tower and the retracted position; determining when the needle has reached a target region; and adjusting the voltage to move the needle towards the retracted position.

Alternatively, the method further comprises receiving a user input of the cell type to a controller provided on the apparatus.

Alternatively, the method further comprises applying a voltage to an actuator provided on the injection device, so as to pull the stage towards the tower in a retracted position.

Alternatively, the method further comprises moving the injection device to within the defined range of the cell-trap, wherein a camera provided on the apparatus is programmed to determine if the injection device is within the defined range. Alternatively, the camera on the apparatus is programmed to determine if the injection device is within the defined range of a periphery of the cell trap.

Alternatively, the actuation data is selected from a group consisting of a record target voltage, a target vertical actuation displacement, a point of penetration, a point of poking, a Voltage-Displacement characteristic curve distortion, and combinations thereof.

In another embodiment, a non-transitory computer-readable medium in which a program is stored for causing a computer to perform a method for controlling a cell injection device is provided, the method comprising: providing an apparatus comprising a cell injection device, a cell trap, and a storage device, the cell injection device comprising a tower, a stage, and a needle, wherein the needle is mounted on the stage; identifying a cell type to be injected; retrieving actuation data from the storage device; applying a voltage so as to pull the stage towards the tower in a retracted position; moving the cell injection device to within a defined range of the cell-trap configured to house a cell type; applying a varying target actuation voltage based on retrieved actuation data to allow the stage and mounted needle to be forced away from the tower and the retracted position; determining when the needle has reached a target region; and adjusting the voltage to move the needle towards the retracted position.

Alternatively, the method further comprises receiving a user input of the cell type to a controller provided on the apparatus.

Alternatively, the method further comprises applying a voltage to an actuator provided on the injection device, so as to pull the stage towards the tower in a retracted position.

Alternatively, the method further comprises moving the injection device to within the defined range of the cell-trap, wherein a camera provided on the apparatus is programmed to determine if the injection device is within the defined range. Alternatively, the camera on the apparatus is programmed to determine if the injection device is within the defined range of a periphery of the cell trap.

Alternatively, the actuation data is selected from a group consisting of a record target voltage, a target vertical actuation displacement, a point of penetration, a point of poking, a Voltage-Displacement characteristic curve distortion, and combinations thereof.

BRIEF DESCRIPTION OF THE DRAWINGS

Additional and further aspects of the present invention will be apparent to the reader from the following description of embodiments, given in by way of example only, with reference to the accompanying drawings in which.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

The following description of various embodiments is exemplary and explanatory only and is not to be construed as limiting or restrictive in any way. Other embodiments, features, objects, and advantages of the present teachings will be apparent from the description and accompanying drawings, and from the claims.

As used herein, the terms "comprise", "comprises", "comprising", "contain", "contains", "containing", "have", "having" "include", "includes", and "including" and their variants are not intended to be limiting, are inclusive or open-ended and do not exclude additional, unrecited additives, components, integers, elements or method steps. For example, a process, method, system, composition, kit, or apparatus that comprises a list of features is not necessarily limited only to those features but may include other features not expressly listed or inherent to such process, method, system, composition, kit, or apparatus.

Figure 1:
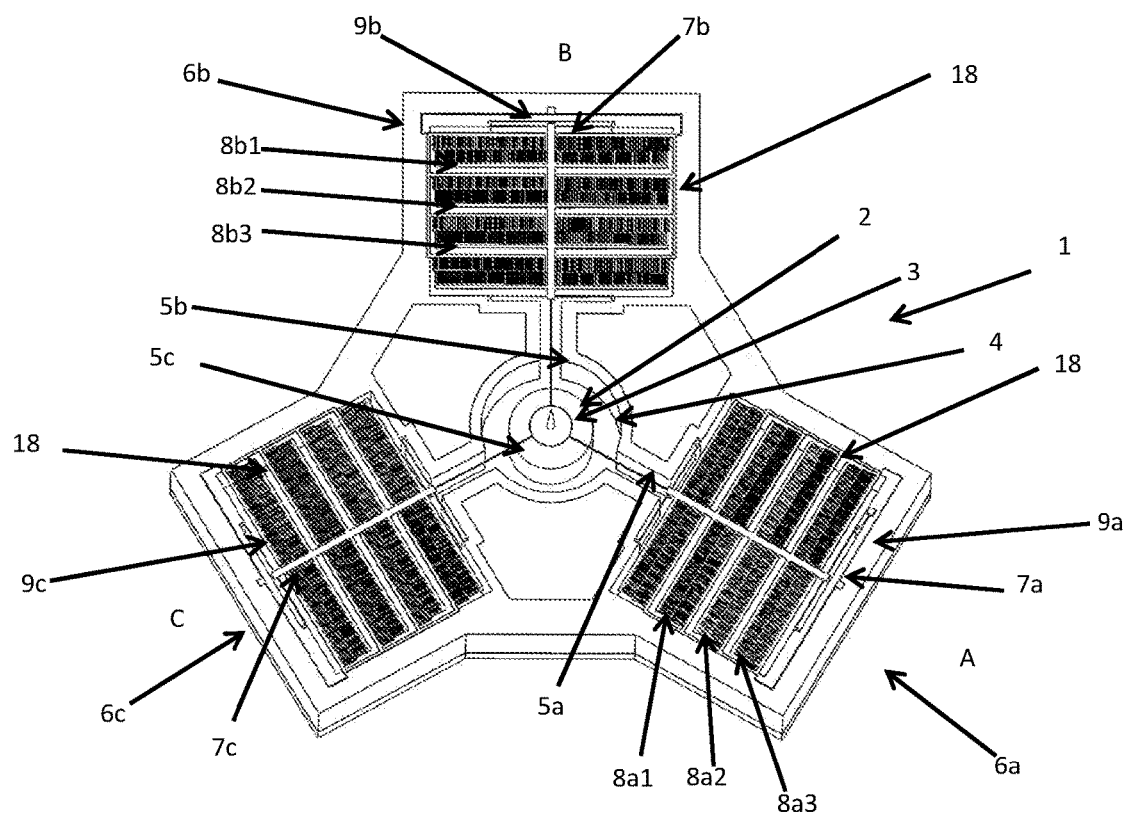
FIG. 1 illustrates a single unit actuator controlled and calibrated for biological cell injection, in accordance with various embodiments.

FIG. 1 illustrates a nanorobot or microrobot in the form of a single-unit needle manipulator 1 which is included in an array of needle manipulators, in accordance with various embodiments, the features of which can be used as illustrated or in combination with other embodiments disclosed herein.

Figure 2:
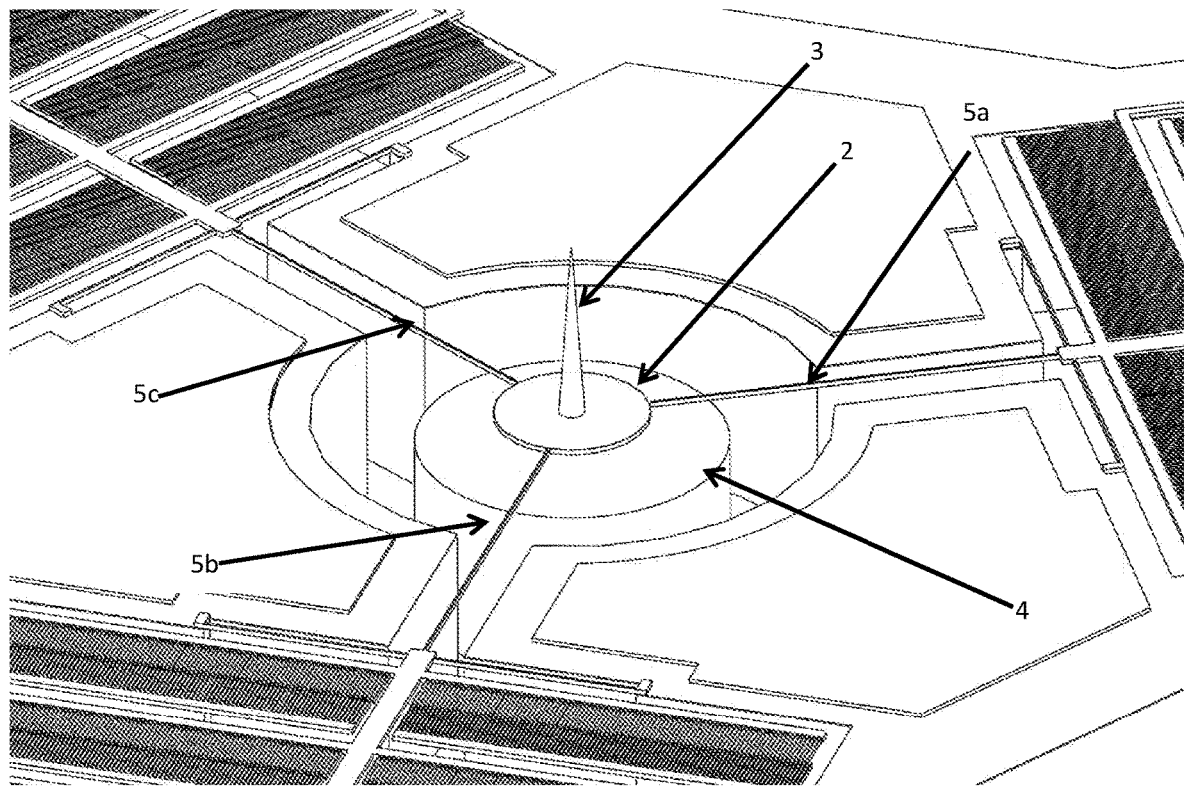
FIG. 2 illustrates a closer view of a single unit actuator controlled and calibrated for biological cell injection, in accordance with various embodiments.

FIG. 2 illustrates a central part of the single-unit needle manipulator, such as that illustrated, for example, in FIG. 1.

The single-unit manipulator 1 has a manipulation stage 2 on which a needle 3 is mounted. Needle 3 can be of a type suited to penetrate an object or cell to deliver, or inject, an agent to the object or cell interior. The injected object or cell may be a biological cell, wherein needle 3 can be of a type suited to penetrate biological cells to deliver, or inject, an agent to the cell interior and/or cell nucleus.

The stage 2 can be located above a tower 4 which can be electrically charged relative to the stage 2 to apply electrostatic forces to the stage 2. The stage and tower may be referred to collectively as a parallel-plate actuator, wherein the opposing surfaces on the stage and tower are electrostatically charged when a voltage is applied across them. Electrostatic forces between the tower 4 and stage 2 can actuate the stage 2 in a Z-axis.

As will be described in detail below in reference to FIG. 3, Z-axis actuation may be the only actuation needed to provide the movement necessary to affect appropriate cell or object penetration by needle 3.

If FIG. 1, the Z-axis can be considered the central axis of the tower 4. The stage 2 can also be actuated in different axes lying in an X-Y plane, in the plane of the manipulator 1 as shown in FIG. 1, by tethers 5a, 5b and 5c. Stage 2 can be configured to manipulate a needle 3 suitable for penetration of objects on this scale of a biological cell. As such, the stage 2 may be referred to as a micro-stage or nano-stage.

The tethers 5a, 5b and 5c tether the stage 2 to actuators 6a, 6b and 6c respectively. The actuators 6 can be located so that forces transferred by the tethers 5 can be in three different axes in the X-Y plane. Each tether 5a/5b/5c can apply tensile forces. Actuators 6 can serve to apply forces from three different directions A, B and C. For example, the actuators 6 can be arranged at 120° intervals about stage 2.

Tether beams 7a, 7b and 7c of actuators 6a, 6b and 6c can connect each of tethers 5a, 5 b and 5c to three support beams 8. The support beams 8 support comb-features, or comb-like electrostatic actuators 18. In this embodiment the actuator 6a has support beams 8a1, 8a2, and 8a3. Actuators 6a and 6c similarly have support beams 8b1/8b2/8b3 and 8c1/8c2/8c3 respectively.

Electrostatic comb features 18 can be located in the same plane as the support beams 8 shown, for example, in FIG. 1. The comb-features may be referred to as comb-drive actuators or comb-drives. The comb-features 18 can be configured to apply force on the support beams 7 in the X-Y axis. The parallel-plate actuator including the central micro-stage 2 and the tower 4 underneath it can be configured to apply force on the tethers 5 in the Z axis. The actuators can have a set of comb-features 18 on the support beams 8 and another opposing set of comb-features 18 on the device. The two opposing sets of comb-features can be charged relative to each other to generate an electrostatic force in the X-Y axis, providing a comb-drive. Similarly the opposing micro-stage 2 and the tower 4 of the parallel-plate actuator can be charged relative to each other to generate an electrostatic capacitive force in the Z axis.

Spring-flexure beams 9 (9a, 9b and 9c) connect or anchor beams 8a, 8b and 8c to a substrate 10 of the manipulator 1. Each actuator 6 can apply a force to the stage 2 in its respective direction. Individual control of the forces applied to the stage 2 in the direction of each actuator 6 allows the stage 2 to be actuated so as to manipulate the needle 3. In so doing, tethers 5 can stretch, and movement of the stage 2 can be dependent on stretching, or strain, of the tethers 5 and flexing of the spring-flexure beams 9.

As shown in FIG. 2, for example, the three tethers 5 of the single-unit manipulator connect actuators in three respective directions to a central stage to provide an elastic support structure for the stage 2.

Figure 3A:
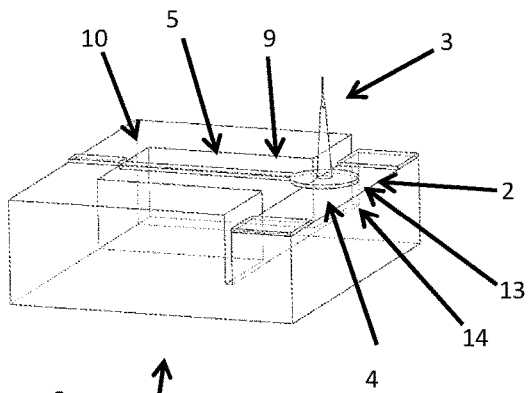
FIGS. 3a to 3c illustrate a parallel plate actuator model representing actuation of a stage of a single unit actuator, in accordance with various embodiments.
Figure 3B:
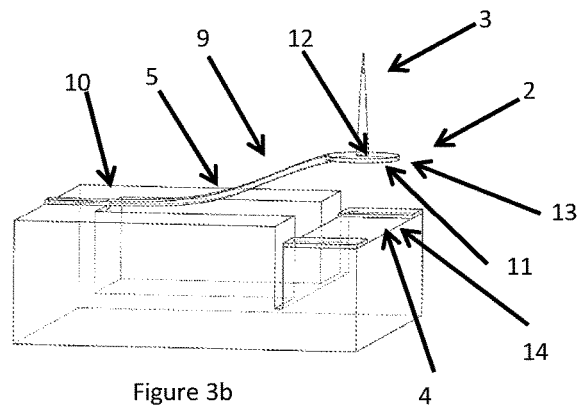
Figure 3C:
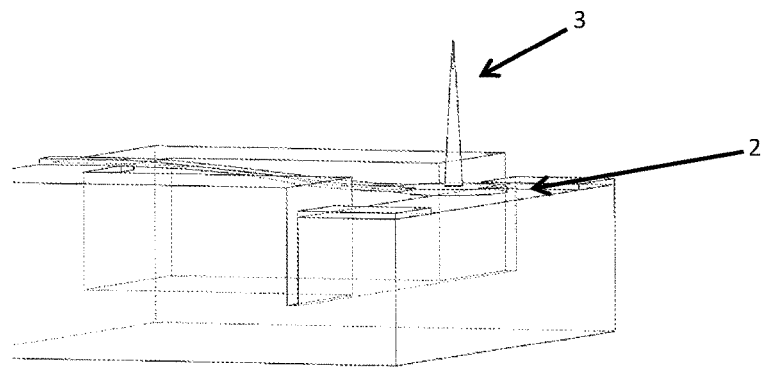

FIGS. 3*a* to 3*c* illustrate an example of a scheme for out of plane Z-actuation of the stage, in accordance with various embodiments, the features of which can be used alone (as illustrated) or in combination with other embodiments disclosed herein. FIG. 3*a* shows the stage 2 and tower 4 as a parallel plate electrostatic actuator formed of a movable surface 13 on the stage and a fixed electrostatic surface 14 on the tower 4. Spring flexure beam 9, which can have the effect of bringing the stage 2 towards a resting position 16 (see FIG. 3*a*) relative to the substrate 10, and above the tower 4. Stretch in the tethers 5 may also contribute to spring effect. Applying a potential across a movable electrostatic surface 11 on the underside of the stage 2 and a fixed surface 12 on the upper side of the tower can displace the stage 2 and needle 3 towards a retracted state 15 (see FIG. 3*c*), relatively closer to the tower 4 and substrate 10. Decreasing the potential can allow the stage 2 and needle 3 to be actuated by restoring force of the tethers 5 and spring flexure beams 9 of actuators 6 relatively away from the tower 4 and substrate 10 towards the resting position 16. This action of decreasing the potential from a retracting potential to actuate the needle away from the substrate 10 will be referred to herein as actuating the needle 3 in a Z axis (see FIG. 3*b* for example of actuating away from the retracted position, and beyond the resting position). If a cell is trapped in proximity to the needle 4, when the stage 2 is in a retracted position injection can be achieved by reducing the potential across the movable and fixed electrostatic surfaces to actuate the stage and needle by reducing the potential to allow the stage to return towards a resting position 16. The degree to which the stage returns towards the resting position from the retracted position is one of many key factors critical to usefully injecting a given type of biological cell. Calibration and control of this actuation according to various embodiments is discussed below.

Figure 4:
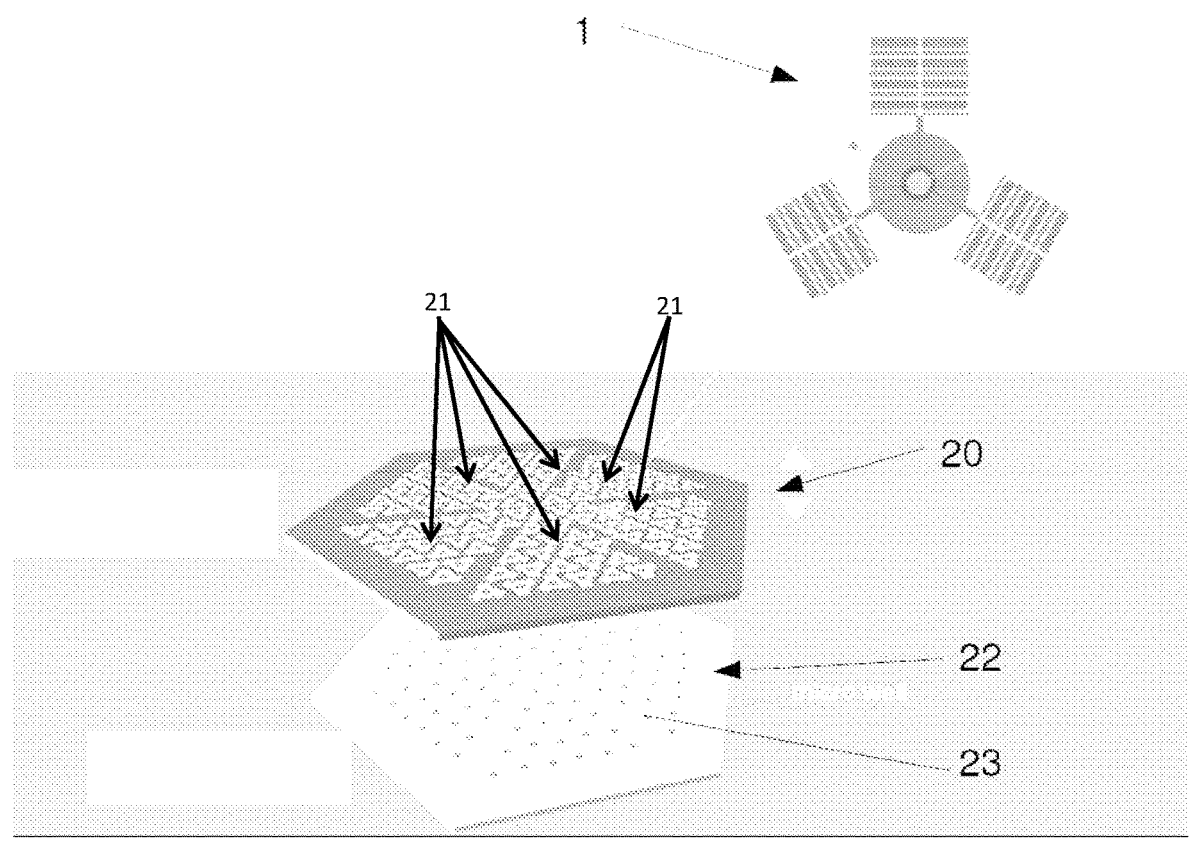
FIG. 4 illustrates a single unit actuator and a corresponding parallel injection device including an array of unit actuators, in accordance with various embodiments.

FIG. 4 illustrates a parallel injection device 20 formed of six arrays 21 of single-unit needle manipulators 1, in accordance with various embodiments, the features of which can be used as illustrated or in combination with other embodiments disclosed herein. The six arrays of FIG. 4 is only an example, and the number of arrays on device 20 can vary as needed. The device 20 can be physically associated with a cell trapping platform 22 which has an array of micro-wells or micro-chambers 23, or cell traps with a cell-trap matching each manipulator in the array. Injecting a cell with a manipulator 1 in the array 21 involves manipulating the stage (and associated needle 3) in the X-Y plane of the device 20 and then actuating the stage 2 in the Z axis.

Figure 5A:
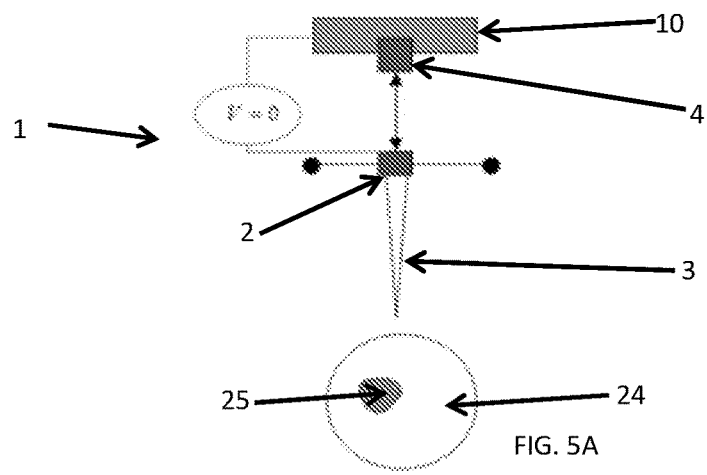
FIGS. 5a to 5f depict a biological cell injection process, in accordance with various embodiments.

FIGS. 5 (5*a* to 5*f*) illustrates a scheme for actuation of a needle 3 of single-unit manipulator 1 for biological cell injection, in accordance with various embodiments, the features of which can be used as illustrated or in combination with other embodiments disclosed herein. FIG. 5*a* depicts the manipulator 1 prior to any operation. As shown, tower 4 is attached to substrate 10. Stage 2 is suspended by tethers 5 that bend to represent stretching, and flexing of spring flexure beams 9 of actuators 6. The needle 3 is shown mounted on the stage 2. FIG. 5*a* also shows a biological cell 24 with a nucleus, or other target within the cell, 25. The nucleus 25 can be penetrated by the needle 3 to deliver a chemical agent (not shown) incorporated into the needle 3. Manipulating or actuating a needle 3 at the micro and nanoscale successfully generally can include overcoming three primary adhesion forces that may have an effect on the process: van der Waals, capillary attraction and electrostatic.

Figures 5B, 5C, 5D, 5E, 5F:
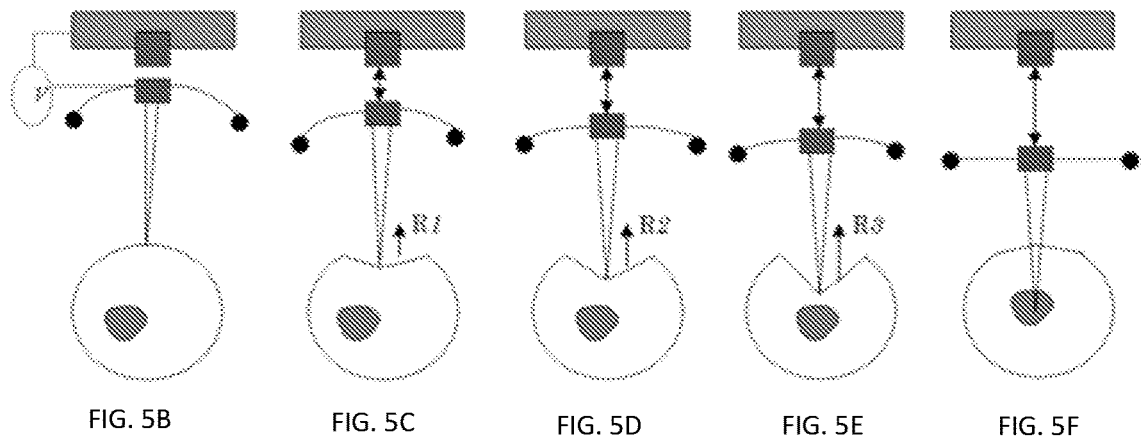

FIG. 5*b* depicts the step on which an electrostatic potential, or voltage, is applied across the fixed and movable surfaces of the tower 4 and stage 2 respectively to retract the stage 2 towards the tower 4 and substrate 10. In conjunction with the retraction, manipulator 1 as part of the device 20 is brought close to the cell 24 held in micro-well 23.

FIG. 5*c* depicts decreasing voltage to V1 to allow the stage 2 to return towards a resting position relatively away from the substrate 10 compared to the state shown in FIG. 5*b*. This step may be understood as actuating the stage 2 and needle 3 in the direction away from the substrate 10 or towards the cell 24. The cell 24 shown as indented by the needle, or poked by the needle. The cell 24 is depicted as exerting a restoring force 26, R1, on the needle 3.

FIG. 5*d* depicts further reduction of the voltage to V2 to actuate the stage 2 and needle 3 further away from a substrate 10. The cell is depicted as exerting the restoring force 26, R2.

FIG. 5*e* depicts the point of further reduction of voltage to V3 with the cell exerting restoring force 26 R3, when the needle 3 first penetrates the cell 24.

FIG. 5*f* depicts the manipulator 1 in the state in which the voltage has been reduced to V0 where the needle 3 penetrates the nucleus 25 of the cell 24. In this particular example the stage 2 is shown as in its resting position. However, the voltage may alternatively be reduced sufficiently for the needle 3 to penetrate the nucleus but not sufficiently to allow the stage 2 to return to its resting position. Among the many factors that can impact voltage level at nucleus penetration, some include, for example, the size and type of cell.

Figure 6:
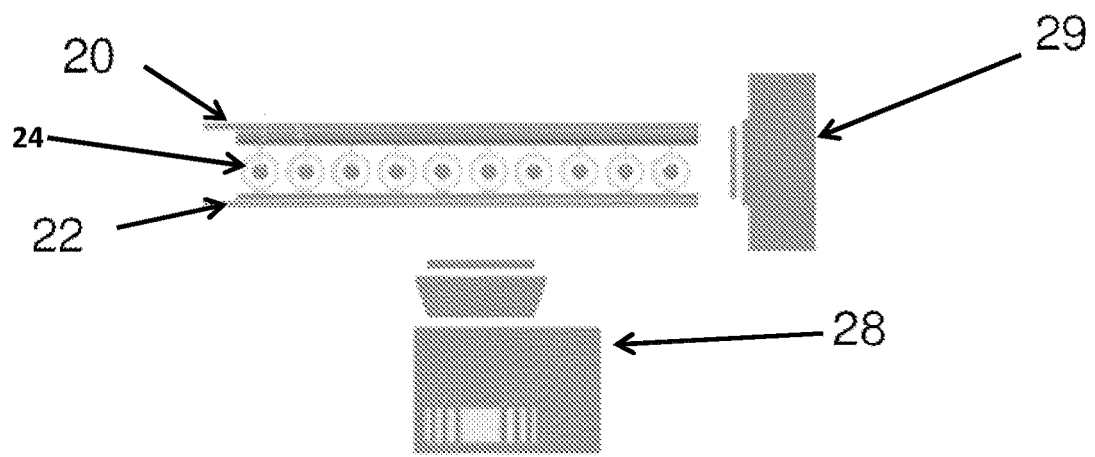
FIG. 6 depicts a parallel injection device and a corresponding cell trap array and cameras, in accordance with various embodiments.

FIG. 6 illustrates an apparatus used in cell injection operations, in accordance with various embodiments, the features of which can be used as illustrated or in combination with other embodiments disclosed herein. A parallel injection device 20 is depicted with opposing cell trapping platform 22 with trapped cells 24. An X-Y camera 28 allows monitoring of the alignment between the parallel injection device 20 and the cell trapping platform 22. The camera 28 can further monitor cells 24, manipulators, and/or movement of the device 20 in the X-Y plane of the device 20. A Z camera 29 allows monitoring of the proximity of the parallel injection device 20 to the cell trapping platform 22.

Figure 7:
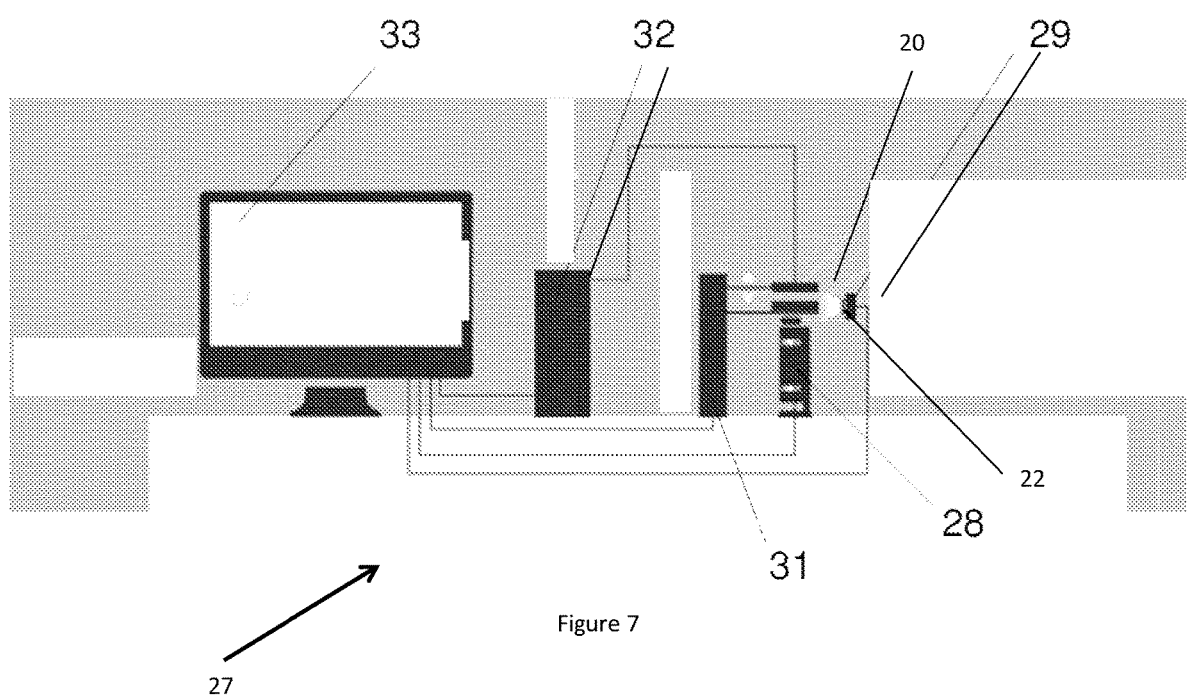
FIG. 7 illustrates a system for control and calibration for biological cell injection, in accordance with various embodiments.

FIG. 7 illustrates a system 27 used in the injection of objects or cells, such as biological cells, in accordance with various embodiments, the features of which can be used as illustrated or in combination with other embodiments disclosed herein. The system has a Z camera 29 (which can be, for, example, a high resolution camera), an inverted microscope with X-Y camera 28, a cell trapping platform 22, a parallel injection device 20, and a macro-stage 31 that is able to move the device 20 macro level towards and away from the cell trapping platform 22. The device 20 can be a parallel array device formed on a substrate. The macro stage can be configured to move the whole device 20. Alternatively, the macro stage can be configured and programmed to move individual manipulators 1. Also illustrated is a caps DAQ system 32 (hereinafter referred to as controller 32) which controls individual single unit manipulators 1, both for X-Y manipulation and for Z actuation. Also shown is a controller running control software 33, which can include a set of instructions stored in on memory media which when executed provides the functionality of the controller.

Computer System

Figure 11:
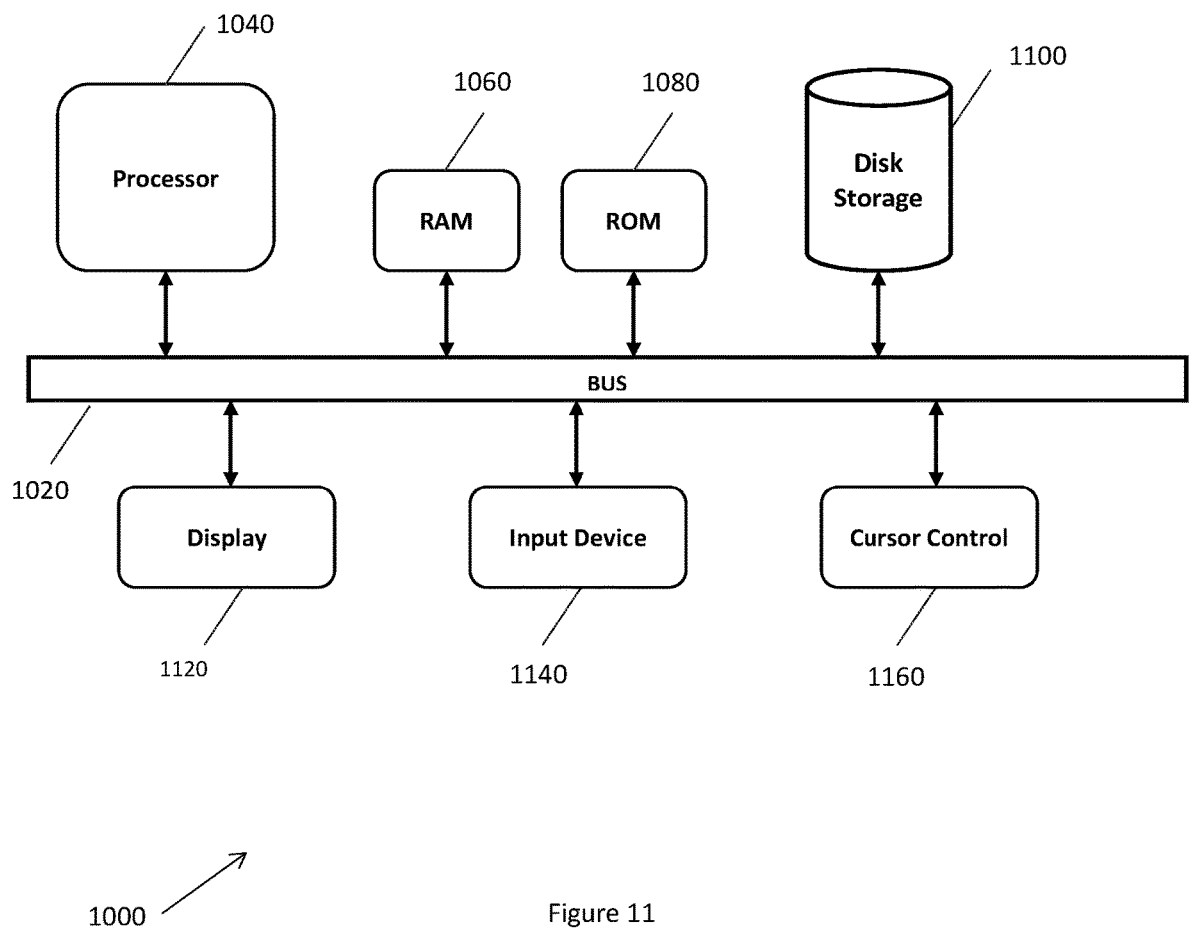
FIG. 11 is a block diagram that illustrates a computer system, in accordance with various embodiments.

FIG. 11 is a block diagram that illustrates a computer system 1000, upon which embodiments, or portions of the embodiments, of the present teachings may be implemented. In various embodiments of the present teachings, computer system 1000 can include a bus 1020 or other communication mechanism for communicating information, and a processor 1040 coupled with bus 1020 for processing information.

In various embodiments, computer system 1000 can also include a memory 1060, which can be a random access memory (RAM) or other dynamic storage device, coupled to bus 1020 for determining instructions to be executed by processor 1040. Memory 1060 also can be used for storing temporary variables or other intermediate information during execution of instructions to be executed by processor 1040. In various embodiments, computer system 1000 can further include a read only memory (ROM) 1080 or other static storage device coupled to bus 1020 for storing static information and instructions for processor 1040. A storage device 1100, such as a magnetic disk or optical disk, can be provided and coupled to bus 1020 for storing information and instructions.

In various embodiments, computer system 1000 can be coupled via bus 1020 to a display 1120, such as a cathode ray tube (CRT) or liquid crystal display (LCD), for displaying information to a computer user. An input device 1140, including alphanumeric and other keys, can be coupled to bus 1020 for communicating information and command selections to processor 1040. Another type of user input device is a cursor control 1160, such as a mouse, a trackball or cursor direction keys for communicating direction information and command selections to processor 1040 and for controlling cursor movement on display 1120. This input device 1140 typically has two degrees of freedom in two axes, a first axis (i.e., x) and a second axis (i.e., y), that allows the device to specify positions in a plane. However, it should be understood that input devices 1140 allowing for 3-dimensional (x, y and z) cursor movement are also contemplated herein.

Consistent with certain implementations of the present teachings, results can be provided by computer system 1000 in response to processor 1040 executing one or more sequences of one or more instructions contained in memory 1060. Such instructions can be read into memory 1060 from another computer-readable medium or computer-readable storage medium, such as storage device 1100. Execution of the sequences of instructions contained in memory 1060 can cause processor 1040 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 1040 for execution. Such a medium can take many forms, including but not limited to, non-volatile media, volatile media, and transmission media. Examples of non-volatile media can include, but are not limited to, optical, solid state, magnetic disks, such as storage device 1100. Examples of volatile media can include, but are not limited to, dynamic memory, such as memory 1060. Examples of transmission media can include, but are not limited to, coaxial cables, copper wire, and fiber optics, including the wires that comprise bus 1020.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 1040 of computer system 1000 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein including flow charts, diagrams and accompanying disclosure can be implemented using computer system 1000 as a standalone device or on a distributed network of shared computer processing resources such as a cloud computing network.

Figure 8:
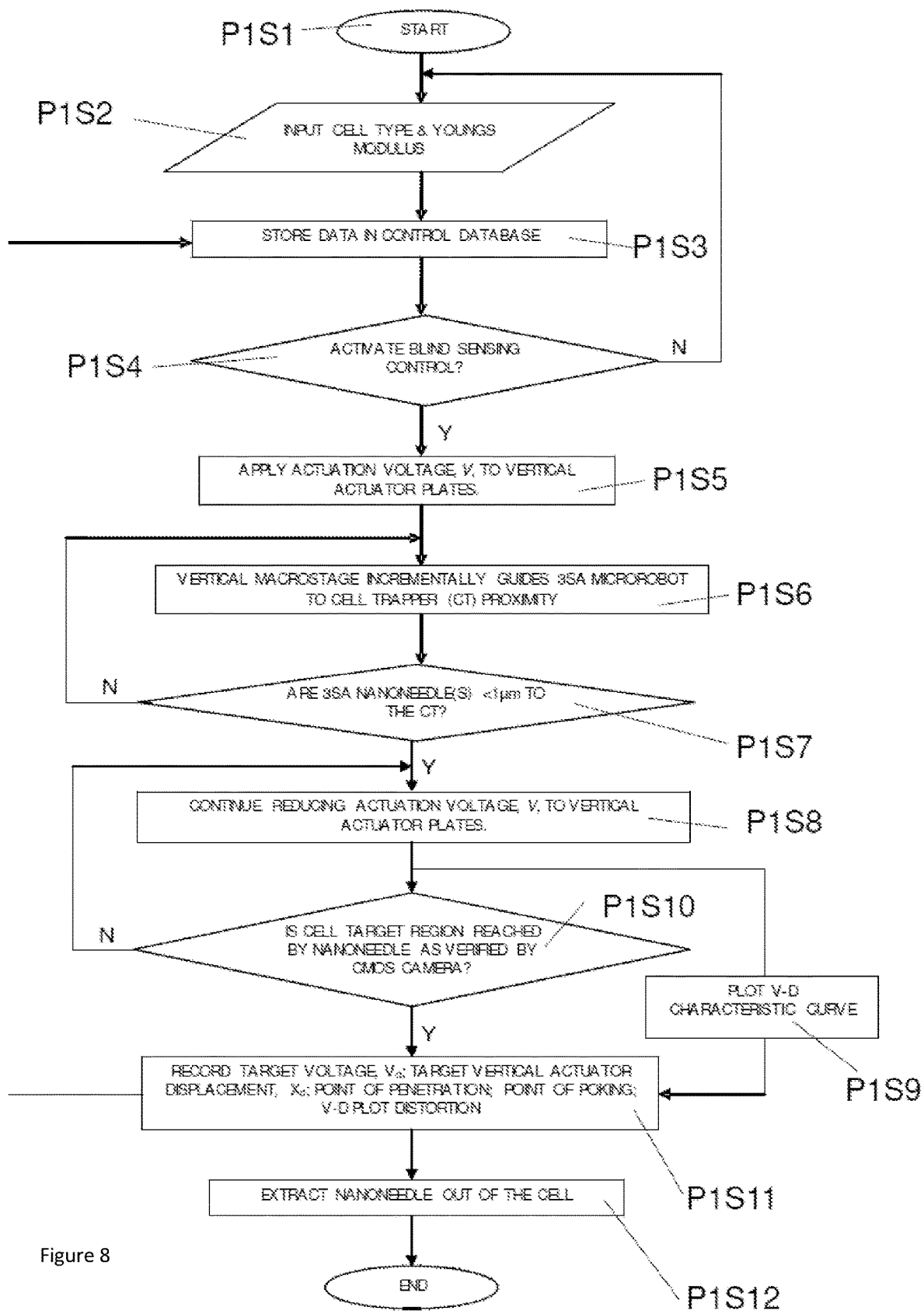
FIG. 8 illustrates a calibration process for biological cell injection, in accordance with various embodiments.

FIG. 8 illustrates an example of a process carried out by a single unit manipulator 1 in a calibration apparatus, which could be part of system illustrated in FIG. 7, in accordance with various embodiments, the features of which can be used as illustrated or in combination with other embodiments disclosed herein. The process can be for determining target voltage potentials to apply to the tower 4 to actuate needle 3 in the Z-axis by targeting the Z-displacement, so as to inject a target, such as a nucleus 25, within a given type of biological cell 24. The process of FIG. 8 is carried out by a single unit manipulator only by way of example. The process can be used by parallel injection device 20 of the system illustrated, for example, in FIG. 7.

The start of the process is shown as step P1 S1, using the convention P1 S1 to denote Process 1 Step 1.

At P1 S2, the controller 32 of the system 27 receives user inputs from operator carrying information on a type of cell and a Young's modulus for the cell wall.

At P1 S3, the controller stores data carrying information from P1 S2. As described later, data carrying information can include information on target voltages and target Z-displacements as well as other information is stored at P1 S3.

At P1 S4, the controller 32 receives inputs from an operator identifying whether a calibration process is required to determine target voltages and target Z-displacements. This may be referred to as a blind sensing process. The software will check if the blind sensing is to be activated. If yes, then the actuation voltage will be applied to parallel arrays of towers individually. If no, then the algorithm will initiate the z control process from the start. There can be multitude of reasons regarding the termination of the blind sensing control and re-start such as error in recording the cell types or external noise affecting the macro and micro-alignment of the system among others.

At P1 S5 a retraction voltage is applied to the tower to establish an electrostatic potential across the tower 4 and stage 2 to retract the needle as shown, for example, in FIG.

5*b*. From this retracted state any reduction in voltage applied to the tower 4 will actuate the stage 2 under restoring force of the tethers 5 and spring flexure beams 9 of actuators 6.

At P1 S6 the macro stage incrementally guides the single unit manipulator 1 towards the cell, which can be provided in a cell trapping platform 22. P1 S7 determines, using the camera 29, whether the manipulator 1 is within a defined range i.e. less than 1 µm of the cell trapping platform 22. In process illustrated by FIG. 8, the controller 32, using the camera 29, determines whether the manipulator 1 is within, for example, one micro-meter of the cell trapping platform 22. If the range is satisfied, then the algorithm continues to the subsequent step. Else, it will go back to the previous step and instruct the macro stage to further incrementally guide the manipulator 1 until the proximity condition is satisfied. This is critical due to the non-visual nature of the controller 32 for vertical manipulation. In the parallel architecture with a plurality of manipulators 1, controller 32, using the camera 29, can determine whether the plurality of manipulators 1 are within, for example, one micro-meter of the cell trapping platform 22 (sub-micron proximity condition).

Alternatively, the camera 29 will verify the sub-micron proximity condition for the cells on the periphery of the cell trapper. In this circumstance, for the cells in the internal sections of the cell trapping platform 22, the controller will act based on the statistical confidence data of the number of the cells that can be manipulated at a time by a single parallel architecture chip.

At P1 S8 the controller 32 will continue reducing the actuation voltage in the parallel-actuator plate, thereby, the needle starts gradually coming back to its original position due to the decrease in electrostatic force between the two plates of the vertical actuator of the manipulator 1. The actual displacement is measured using a single/double-beam laser interferometer at room temperature. There is a continuous change in the applied voltage between the two plates and therefore the change in distance between these plates.

Figure 9:
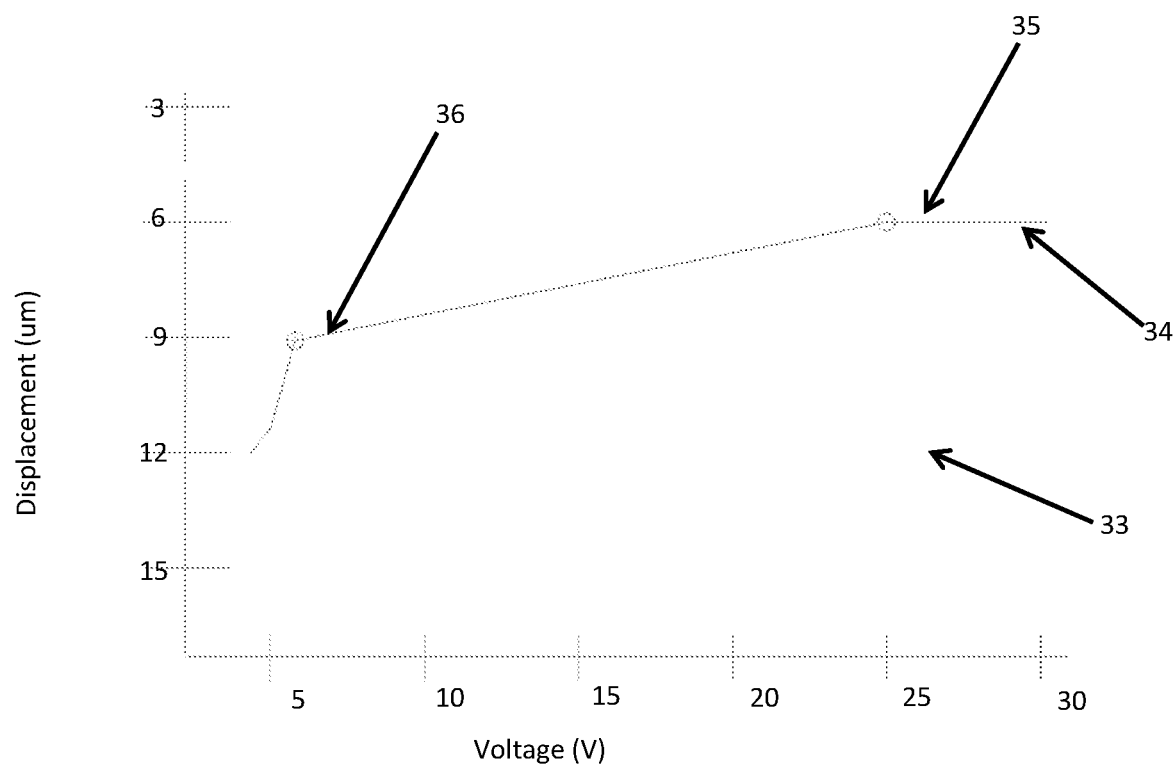
FIG. 9 depicts a relation between displacement of a stage of the single unit actuator showing characteristics recorded in a calibration process, in accordance with various embodiments.

At P1 S9, while the actuation voltage is reduced incrementally, the corresponding voltage-displacement characteristic curve is plotted as shown, for example, in FIG. 9. The plot primarily relies upon two variable parameters, namely change of potential in the parallel-plate actuator in relation to the change of position of the central stage 2 relative to the tower 4 as shown in FIG. 5. The sudden significant decrease in the plot between these two parameters, voltage and displacement, during vertical motion is used as a signature for feedback to the controller 32 to enable the biomanipulation. This change in the plot can be attributed, for example, to the change in stiffness of the cell membrane that is sensed by the nanoneedle. Rather than measuring the force during manipulation (plotting it against time), the voltage-displacement principle illustrated by the FIG. 9 curve allows the measuring of the decrease in voltage to identify the points of penetration and poking into the cell.

At P1 S10, the condition that the needle has arrived at the final cell target region such as the nucleus or mitochondria is verified by, for example, the camera 29 (as shown by the exemplary CMOS camera in FIG. 9) or fluorescent microscopy. If this condition is satisfied, then the algorithm will proceed forward to record actuation data. If not, then the actuation voltage is further reduced incrementally until the final cell target compartment is reached. Once this system is calibrated for a cell type, the relationship between the voltage and displacement is fed into a controller database, such as storage device 1100 of FIG. 11, a priori (discussed below).

At P1 S11, once the manipulation at the target region inside the cell is complete, actuation data such as record target voltage ($V_d$), target vertical actuation displacement ($X_d$), points of penetration and poking, and V-D characteristic curve distortion, are recorded and stored into the controller database, such as storage device 1100 of FIG. 11. This record of data is critical for the parallel manipulation, because similar to xy control, for z tracking, closed-loop control can be used by using error in position signals as feedback to form a closed-loop. This calibrated data will eventually act as a reference input and will employ PID control for achieving the desired voltage, $V_d$, and thereby avoiding overshooting of the nanoneedle.

At P1 S12, the nanoneedle is then pulled out of the cell at a velocity. The velocity can range, for example, between 0.5-2.5 mm sec$^{-1}$. Biological membranes generally stretch elastically only by approximately 2%-4% before they rupture. Cells have an ability to resist fast changes in the membrane tension brought upon by external forces such as needle manipulation in our case. There are numerous tension-sensitive surface area regulation mechanisms that can help the cells resist more dramatic and slower changes in the cellular environment. One example is a small bilayer reservoir that can buffer minor increases in the membrane tension.

The steps P1 S8, P1 S9, P1 S10 and P1 S11 taken together can be referred to as the blind sensing mechanism.

FIG. 9 shows a plot 33 of the relation of voltage, in Volts, versus displacement in micrometres captured at P1 S9 (introduced above). The plot 33 shows a point 36 of gradual decrease in rate of change of displacement with voltage which is characteristic of the needle 3 beginning to poke a cell 24 as shown in FIG. 5*c*. The plot 33 also shows a point 35 of further decrease in the rate of change of displacement with voltage which is characteristic of the needle 3 beginning to penetrate cell 24 as illustrated in FIG. 5*e*. The controller 32 recognises these points 36 and 35 by relating data defining the relation of voltage to displacement against characterisation data.

Figure 10:
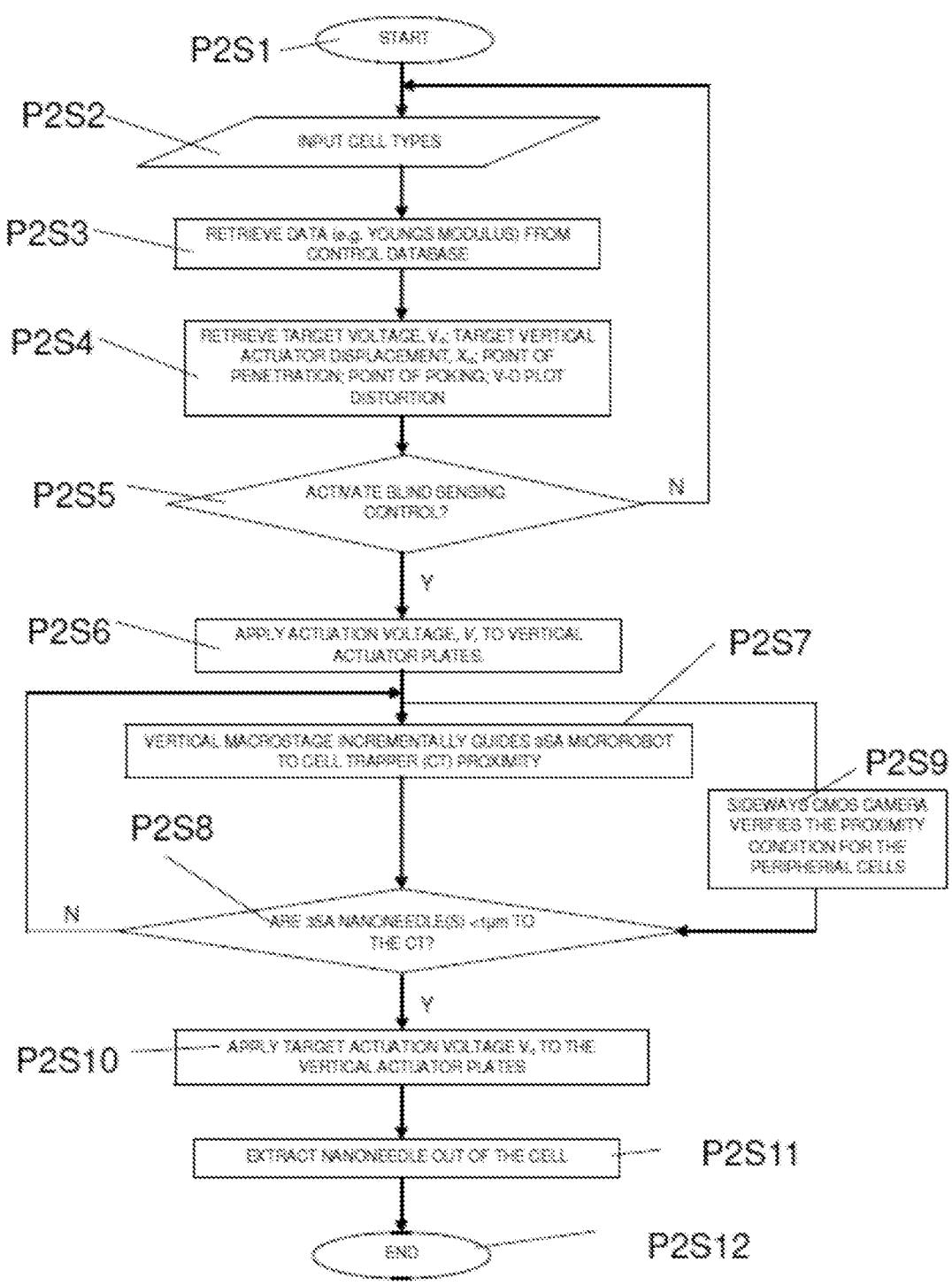
FIG. 10 illustrates a control process for biological cell injection, in accordance with various embodiments.

FIG. 10 shows an example of a process P2 for controlling a parallel injection device 20 (or cell injection device), in accordance with various embodiments, the features of which can be used as illustrated or in combination with other embodiments disclosed herein. The process of FIG. 10 is carried out by a single unit manipulator only by way of example. The process can be used by parallel injection device 20 of the apparatus/system illustrated, for example, in FIGS. 6 and 7. The process starts at P2 S1.

At P2 S2, the controller 32 receives inputs from an operator identifying a cell type to be injected by a single unit manipulator 1. The cell type may be identified for each single unit manipulator 1 in the parallel injection device 20 to allow different types of cells, for example, to be injected in parallel injection operations.

At P2 S3, the controller 32 retrieves data stored in association with for an identified cell type, including Young's modulus of the cell type.

At P2 S4, the controller 32 retrieves data carrying the following additional information: target voltage to be applied to tower 4, target vertical displacement of stage 2 captured at P1 S5 in FIG. 8, the displacement and/or voltage at which the needle 3 begins to penetrate the cell 24 captured at steps P1 S6 to P1 S8 and the displacement versus voltage plot captured at P1 S9, for example. Data used to identify displacement versus voltage plot characteristics for poking and penetration can also be retrieved.

At P2 S5, the controller 32 determines whether a cell injection operation should start. Controller 32 can determine this by inputs from an operator received by the controller 32. The controller can check if the blind sensing is to be activated. If yes, then the actuation voltage can be applied to parallel arrays of towers 4 individually. If no, then the algorithm can return to P2 S2 to initiate the z control process from the start. There can be a multitude of reasons for termination of the blind sensing control and re-start. These can include, for example, error in recording the cell types, external noise affecting the macro and micro-alignment of the system, or other examples.

At P2 S6 voltages are applied to the tower 4 to retract the stage 2 to the state shown, for example, in FIG. 5b. By extension, with potential difference applied to all of the manipulators 1 in the parallel injection device 20, the voltage is applied to each of the tower 4 of each of the manipulators 1 to retract each of the stages 2. 3SA microrobot is an example of injection device 20.

At P2 S7, the macro stage 31 incrementally guides the parallel injection device 20 towards the cell trapping platform 22 while the Z-camera 29 is used by the controller 32 to monitor the proximity of the parallel injection device 20 to the cell trapping array (or platform) 22. Alternatively, the camera 29 will verify the proximity of the parallel injection device 20 on the periphery of the cell trapping array 22. In this circumstance, for the cells in the internal sections of the cell trapping platform 22, the controller will act based on the statistical confidence data of the number of the cells that can be manipulated at a time by a single parallel architecture chip.

At P2 S8 and P2 S9, the controller 32 determines whether the parallel injection device 20 is suitably close to the cell trapping array 22 and returns the process to P2 S7 otherwise. The Z camera 29 provides suitable video data at P2 S9 for this decision. The sub-micron range proximity information is validated by the Z camera 29 placed sideways. In the parallel architecture with a plurality of manipulators 1, controller 32, using the camera 29, can determine whether the plurality of manipulators 1 are within, for example, one micrometer of the cell trapping platform 22 (sub-micron proximity condition).

Alternatively, the camera 29 will verify the sub-micron proximity condition for the cells on the periphery of the cell trapper. In this circumstance, for the cells in the internal sections of the cell trapping platform 22, the controller will act based on the statistical confidence data of the number of the cells that can be manipulated at a time by a single parallel architecture chip.

Due to the nature of non-visual sensing of the system and mechanism of the controller 32 that can detect the manipulation through some physical change, the sub-micron proximity between the parallel arrays of needles and their corresponding cells is critical. In addition, because the Z movement of the needles has a range such as, for example, between 5-10 μm, the satisfaction of the proximity condition as a pre-requisite allows most of the cells to be physically manipulated. If the range is satisfied, then the algorithm continues to the subsequent step. Else, it will go back to P2 S7 and will instruct the macrostage to further incrementally guide the parallel architecture chips until the proximity condition is satisfied.

At P2 S10 the target actuation voltage of P2 S4, for the cell type selected at P2S2, is retrieved by the controller 32 and, for the specific manipulator 1 being controlled, applied to the tower 4 to actuate the stage 2 and needle to a target so the needle 3, for example, penetrates the target. This is the target voltage which actuates the stage and needle to the target, such as nucleus 25, of the particular cell type selected at P2 S2 as illustrated, for example, in FIG. 5f.

The blind sensing mechanism is employed during this step when the cell manipulation actually occurs. Similar to the XY controller, for Z tracking, we use closed-loop control by using error in position signals as feedback to form a closed-loop. The controller accepts a desired position, $X_d$, as the reference input and employs PID control for achieving the desired voltage, $V_d$, and therefore avoids overshooting of the needle. As discussed earlier, the calibrated values of $X_d$ and $V_d$ are pre-programmed into the controller 32 for different types of cells. The voltage is now gradually reduced (V to V1 to V2 to V3 to $V_d$), which decreases the electrostatic force (E to E1 to E2 to E3 to $E_d$) between the plates gradually as shown, for example, in FIGS. 5c to 5e. As the controller 32 starts reducing the actuation voltage for each needle, they start gradually coming back to their original position due to the decrease in electrostatic force between the two plates of the parallel injection device 20. As needles start coming out of their retracted state, they gradually penetrate through the cell membranes because of the vertical stiffness of the manipulators 1 and the decreasing parallel-plate electrostatic force, until they poke through these membranes completely and are in the target site inside the cells. The primary purpose of the controller 32 is to enable manipulation using the blind sensing and prevent overshooting of the needles during the manipulation process.

There is a continuous change in the applied voltage between the two plates of the parallel injection device 20 and therefore the change in distance between these plates. Therefore, $X_d$ and $V_d$ are continually changing to guide the arrays of needles to the specific target position inside these arrays of cells. The error, $X_{diff}$ in z positioning precision is calculated from the estimator that uses the blind sensing model by comparing the measured position, $X_m$ with the desired position, $X_d$. The PID controller calculates the desired voltage to drive the needles in the parallel architecture to the desired vertical position in Z axis. Once the needles are inside the cell, depending on the cell organelle to be manipulated such as nucleus, the needles might undergo another motion, resulting in another subsequent decrease in the V-D plot as shown as an example in FIG. 9, confirming the poking through the second cellular organelle.

It is the change in the plot of the voltage-displacement tracking curve that identifies penetration and subsequent poking through the cell membranes. This change is the alteration of the cell membrane stiffness sensed by the needle during vertical manipulation and is reflected in the force-deflection curve as shown in FIG. 9. This is primarily a model-based feedback employing a blind control scheme and therefore the precision of the position of the needle in a Z coordinate frame can depend on the accuracy of this blind model. Based on electrostatic force law, the output motion of the central stage 2 relative to the bottom tower 4 is expected to be proportional to the square of the actuation voltage, $U_{x,y,z} \propto V^2$. Due to this electrostatic nature, this blind sensing scheme is a linear system with deterministic behaviour. Nonetheless, immediately following the poking into the cell, the behaviour becomes non-linear due to the vibration induced into the system with the rupture of the cell membrane.

A P2 S11 the voltage on the tower 4 is adjusted to retract the needle 3 as illustrated in FIG. 5b to remove the needle 3 from the cell 24. The process ends at P2 S12.

Further detail on the calibration process, such as the one exemplified in FIG. 8, in accordance with various embodiments, will now be given in reference to steps in FIG. 8.

The blind sensing mechanism of P1 S8, P1 S9, P1 S10 and P1 S11 can produce different displacement versus voltage plots, and plot characteristics, for different types of cell due to factors such as, for example, cell size, membrane thickness and Youngs Modulus of the membrane (elasticity). Therefore, the controller can request inputs to identify data carrying information such as cell type and the corresponding Youngs Modulus (E), for example, as noted in Table 1.

TABLE 1

| Cell Type | E(kPa) |
|---|---|
| Endothelial cells | |
| HUVEC | 10-11 |
| BPAEC | 0.2-2.0 |
| Leukocytes | |
| Leukemia myeloid cells (HL60) | 0.2-1.4 |
| Leukemia lymphoid (Jurkat) cells | 0.02-0.08 |
| Neutrophils | 0.2-0.07 |
| Osteoblasts | 0.3-20.0 |
| Astrocytes | 2-20 |
| Fibroblasts | 4-5 |
| Migrating 3T3 cells | 3-12 |
| L 929 | 4-5 |
| Epidermal keratocytes | 10-55 |
| Platelets | 1-50 |
| Skeletal muscle cells | |
| Murine $C_2C_{12}$ myoblasts | 11-45 |
| Myofibrils | 40-45 |
| Erythrocytes | 14-18 |

For example, injecting Leukaemia myeloid cells (HL60), with an E value of 0.2-1.4 kPa generally will require comparatively less force in the Z-axis compared to Erythrocytes, with an E value of 14-18 kPa. Due to such wide differences in E values, individual cells, from the ones being widely used in research and clinical studies to the more rare ones such as Circulating Tumour Cells (CTCs), should be calibrated for injection.

Once the cell type is entered, the controller can store data carrying this information in a control database such as storage device 1100 of FIG. 11. The control database also contains data carrying information for actuation such, for example, as target voltage, displacement, points of first penetration and first poking, among others. This will be subsequently retrieved for parallel injection operations. The displacement versus voltage plot is retrieved as well.

The controller can also check at a step such as, for example, at P1 S4 whether the blind sensing mechanism of P1 S8, P1 S9, P1 S10 and P1 S11 is to be activated. If yes, then an actuation voltage will be applied to the tower. If no, then the algorithm will return the process to P1 S2. For example if there is an error in recording the cell type to be manipulated or the system macro-alignment has been compromised due to some external noise, then the calibration will be terminated. In some embodiments, steps such as scanning for nuclei, system macro-alignment and fine X-Y axis alignment of the needles can occur before the calibration activated.

A macromanipulator, such as MP-285 Sutter Instrument Co., with a coarse submicron resolution of 0.2 μm and almost 40 nm fine resolution, can be used to connect the parallel architecture chip 20 using a fixture to hold it firmly in place. Before the vertical movement of the entire chip occurs, a actuation voltage is applied at a step such as P1 S5 to the tower of the manipulator. The central stage will be already at a particular potential applied during the fine X-Y alignment of nanoneedles. A retraction voltage can exert an attractive electrostatic force on the central stage and pull it back toward a tower and substrate.

When the stage and needle are in retracted state, for example, the parallel injection device can undergo a coarse macro-movement at P1 S6 while the macromanipulator incrementally brings the device down vertically so the needles are in close proximity of the cells. The calibration process may require that the gap between the needle tip and the upper cell membrane be within sub-micron range (e.g., less than 1 μm) leading to the next step.

The sub-micron range proximity information can be verified at a step such as P1 S7 by a camera such as, for example, a high-resolution CMOS camera. If the range is verified, then the controller continues to the subsequent step such as P2 S8. Otherwise, the controller will go back to the previous step such as P2 S6 and instruct the macromanipulator to further incrementally guide the device 20 (e.g., a 3SA manipulator) until the proximity condition is satisfied. In the parallel architecture with a plurality of manipulators 1, controller 32, using the camera 29, can determine whether the plurality of manipulators 1 are within, for example, one micrometer of the cell trapping platform 22 (sub-micron proximity condition).

Alternatively, the camera 29 will verify the sub-micron proximity condition for the cells on the periphery of the cell trapper. In this circumstance, for the cells in the internal sections of the cell trapping platform 22, the controller will act based on the statistical confidence data of the number of the cells that can be manipulated at a time by a single parallel architecture chip. This is important due to the non-visual nature of the controller for vertical manipulation.

At a step such as P1 S8, the controller can gradually reduce the actuation voltage on the tower, allowing the needle to start gradually coming back to its resting position due to the decrease in electrostatic force between the stage and tower. Displacement of the stage from the tower, or from a resting position or from retracted position, can be measured by various means including, for example, a single or double-beam laser interferometer at room temperature. There can also be a continuous change in the applied voltage between the two plates and therefore the change in distance between these plates.

Moreover, when using a single unit manipulator for calibration, the condition where the needle has arrived at a given final cell target region, such as the nucleus or mitochondria, can be verified by, for example, a camera (such as, for example, a hi-res CMOS camera), or fluorescent microscopy. If this condition is satisfied, then the algorithm can proceed to a step such as P1 S11 to record actuation data. If not, the process can loop back such that the actuation voltage can be further reduced in a step, such as P1 S8 (see loop between steps P1 S8 and P1 S10, for example, on FIG. 8), incrementally until the final cell target compartment is reached.

Once this system is calibrated for a cell type, the relationship between the voltage and displacement recorded at a step, such as P1 S9, can be fed into the controller database, such as storage device 1100 of FIG. 11. While the actuation voltage is reduced incrementally, the corresponding voltage-displacement characteristic curve is plotted at P1 S9 (see FIG. 9 for example). The plot (such as that provided in FIG. 9) primarily relies upon two variable parameters, namely, change of potential on the tower and stage, in relation to the change of position of the stage relative to the tower as shown, for example, in FIG. 1. A sudden significant decrease in the plot between these two parameters, voltage and displacement, during vertical motion can be used as a signature characteristic for feedback to the blind sensing controller to enable the injection. A defined characteristic observed in the plot or development of the plot in real-time can be used as a feedback signature or prompt. This change in the plot can be attributed, for example, to the change in stiffness of the cell membrane that is sensed by the actuated needle. Rather than measuring the force during manipulation (plotting it against time), the controller can measure the decrease in voltage, or a defined characteristic in the voltage vs displacement, to identify points of penetration and poking into the cell.

Once the manipulation and actuation of the needle to target region inside the cell is complete, calibration data carrying actuation information such as, for example, record target voltage ($V_d$), target vertical actuator displacement ($X_d$), points of penetration, points of poking, and V-D characteristic curve distortions, are recorded and stored into the controller database, such as storage device 1100 of FIG. 11. This record of data can be used by the controller for manipulation and actuation of needles in an injection operation. This information can be particularly useful for parallel injection operations. Similar to X-Y control, for Z-tracking, the controller can use closed-loop control by using error in position signals as feedback to form a closed-loop. This calibration data can provide a reference input for the controller and can employ PID control for achieving the desired record target voltage, $V_d$ thereby avoiding overshooting of the needle.

The needles can be pulled out of the cell in a step such as P1 S11 at a velocity in the range 0.5-2.5 mm sec$^{-1}$. Biological membranes typically stretch elastically by approximately 2%-4% before they rupture. Cells have an ability to resist fast changes in the membrane tension brought upon by external forces such as needle manipulation in our case. This may be due, for example, to a small bilayer reservoir that can buffer minor increases in the membrane tension. Moreover, there are other known tension-sensitive surface area regulation mechanisms that can help the cells resist more dramatic and slower changes in the cellular environment.

A biological cell injection operation process according to various embodiments will now be described. The control software receives inputs identifying cell types to be injected at a step such as P2 S2. Depending on the type of operation, either a single cell type (in parallel) or multiple cell type information can be entered.

Cell data carrying information such as Youngs Modulus for the cell membrane, membrane thickness, and cell size can be retrieved from the control database such as storage device 1100 of FIG. 11. This cell data are for Z-motion and injection.

Calibration data can be retrieved at a step such as P2 S4 for different cell types and the relationship between the voltage and displacement can be fed into the controller, a priori. The calibrated values of $X_d$ and $V_d$ can be pre-programmed into the controller for different types of cells. Thus, for a particular cell type, such as leukaemia myeloid cells (HL60) with Young's modulus of the membrane between 0.2-1.4 kPa (Table 8.1), the system can be calibrated and $X_d$ and $V_d$ can be used as parameters to drive the needle to a desired position inside the cells, such as nucleus. Moreover, data pertaining to multiple cell types can be retrieved simultaneously.

The controller can also be configured to check, at a step such as P2 S5, whether a cell is to be injected. If yes, then a retrieved actuation voltage will be applied to parallel arrays of towers individually. If no, then the controller will terminate the blind sensing mechanism and restart the process. There are various reasons that can lead to a termination of the blind sensing control and re-start such as error in recording the cell types or external noise affecting the macro and micro-alignment of the system among others.

As noted above, depending on the check at P2 S5, an actuation voltage can be applied to the towers in a step P2 S6. The stages in each single unit manipulator in the array are already biased during the fine X-Y movement of the needles. The resulting potential difference, therefore, can retract the stages back as shown in FIG. 5*b*. Individual stages can be biased differently based on, for example, the cell type or target regions. Moreover, the individual towers can be differentially biased to maintain a uniform electrostatic gap in the parallel-plate actuators.

A vertical macropositioning stage gripping the chips in their retracted state can then gradually brings them down to close proximity of the cell in a step such as P2 S7. The macrostage can be guided by, for example, a camera such as, for example, a high-resolution Z-camera. As discussed earlier, the condition for the sub-micron gap between the needles and the cells is important. During this entire process, the needles continue to be pre-aligned in the xyz directions.

As the chip is gradually brought down to close proximity to the cell, or plurality of cells, the sub-micron range proximity information can be validated by, for example, a camera such as, for example, a high-resolution CMOS camera, in a step such as P2 S9. For arrays of parallel architecture chips with a plurality of manipulators 1, controller 32, using the camera 29 (e.g, CMOS camera), can determine whether the plurality of manipulators 1 are within, for example, one micrometer of the cell trapping platform 22 (sub-micron proximity condition).

Alternatively, the camera 29 will verify the sub-micron proximity condition for the cells on the periphery of the cell trapper. In this circumstance, for the cells in the internal sections of the cell trapping platform 22, the controller (e.g., z controller) will act based on the statistical confidence data of the number of the cells that can be manipulated at a time by a single parallel architecture chip.

Due to the nature of non-visual sensing of the system and mechanism of the z controller that can detect the injection through some physical change in various embodiments, it is advantageous to be able to determine the sub-micron proximity between the parallel arrays of needles and their corresponding cells. In addition, in some cases, the Z-movement of the needles can be limited in range to, for example, between 5-10 μm. In those cases, the satisfaction of the proximity condition may be a pre-requisite so that most of the cells can be physically manipulated. If the range is verified at a step such as P2 S9, the controller continues to the subsequent step such as S2 P10. Else, it can go back to a step such as P2 S7 and instruct the macrostage to further incrementally guide the parallel architecture chips until the proximity condition is satisfied.

As stated above, a blind sensing mechanism can be employed during a step when the cell injection occurs. Similar to the X-Y controller, for Z tracking, a closed-loop control can use error in position signals as feedback to form a closed-loop. The controller can accept a desired position, $X_d$ as the reference input and can employ PID control for achieving the retrieved voltage, $V_d$, thereby avoiding overshooting of the needle. Calibration data carrying $X_d$ and $V_d$ can be stored by the controller for different types of cells.

As the voltage is gradually reduced (V to V1 to V2 to V3 to $V_d$), electrostatic force decreases (E to E1 to E2 to E3 to $E_d$) between the plates gradually, as shown, for example, in FIGS. 5c to e. As the controller starts reducing the actuation voltage for each needle, they start gradually coming back to their original position due to the decrease in electrostatic force between the two plates of the parallel-plate actuators. As needles start coming out of their retracted state, they gradually penetrate through the cell membranes because of the vertical stiffness of the manipulators and the decreasing parallel-plate electrostatic force, until they poke through these membranes completely and are in the target site inside the cells.

There can be a continuous change in the applied voltage between the two plates and therefore a continuous change in distance between these plates. Therefore, $X_d$ and $V_d$ are continually changing to guide the arrays of nanoneedles to the specific target position inside these arrays of cells. The error, $X_{diff}$, in Z-positioning precision is calculated from an estimator that uses the blind sensing model by comparing the measured position, $X_m$, with the desired position, $X_d$. The PID controller calculates the desired voltage to drive the nanoneedles in the parallel architecture to the desired vertical position in Z axis. Once the needles are inside the cell, depending on the cell organelle to be manipulated, such as a nucleus, the needles might undergo another motion, resulting in another subsequent decrease in the V-D plot, confirming the poking through a second cellular organelle.

The change in the plot of the voltage-displacement tracking curve in some embodiments helps identify penetration and subsequent poking through the cell membranes. This change is the alteration of the cell membrane stiffness sensed by the needle during vertical manipulation and is reflected in the force-deflection curve as shown earlier in FIG. 9. This is primarily a model-based feedback employing a blind control scheme and therefore the precision of the position of the needle in a Z coordinate frame can depend on the accuracy of this blind model. Based on electrostatic force law, the output motion of the stage relative to the tower can be expected to be proportional to the square of the actuation voltage, $U_{x,y,z} \propto V^2$. Due to this electrostatic nature, our blind sensing scheme can be a linear system with purely deterministic behaviour. Nonetheless, immediately following the poking into the cell, the behaviour can then become non-linear due to the vibration induced into the system with the rupture of the cell membrane.

Once the injection is complete, the needles are pulled back from the cells by the vertical macropositioning stage before the next set of injection operation occurs. The velocity of motion of the needles can be around 0.5-2.5 mm sec$^{-1}$. Therefore the frequency associated with this movement can be significantly less compared to the resonant frequencies of the 3SA manipulators. The first resonant frequency of the manipulator as predicted from finite element analysis can be, for example, 12 kHz (in-plane mode for XY) and second resonant frequency can be, for example, 27 kHz (Z mode motion including flexure of comb-finger electrodes). Unless the cell manipulation occurs at a very high rate, closer to the resonant frequencies when dynamic response analysis becomes important, then the movement of the needles are static.

It should be noted that injection of objects or cells other than biological cells can be performed. These objects can include, for example, viruses, liposomes, micelles, reverse micelles, protein capsules, liquid droplets, globular protein complexes, protein-DNA complexes, protein-RNA complexes, protein-cofactor complexes, any object with a discrete volume, or a combination thereof.

RECITATION OF EMBODIMENTS

Embodiment 1

A method of controlling a needle actuator to interact with a cell, the method comprising: providing an actuator comprising a tower, a stage and a needle, wherein the needle is mounted on the stage; applying an electrostatic potential between the tower and the stage to retract the needle; moving the actuator towards the cell; reducing the potential so as to allow the stage and needle to move towards the cell; applying calibration data to detect when the needle has pierced the cell; and reducing the potential further once it has been detected that the needle has pierced the cell.

Embodiment 2

The method of Embodiment 1, wherein the cell is a biological cell.

Embodiment 3

The method of Embodiments 1 and 2, wherein the needle is a micro-needle and the stage is a micro-stage.

Embodiment 4

The method of any of the preceding Embodiments, wherein the cell is held by a cell trap.

Embodiment 5

The method of any of the preceding Embodiments, further comprising applying an electrostatic potential between the tower and the stage to retract the needle towards the stage.

Embodiment 6

The method of any of the preceding Embodiments, further comprising reducing the potential to allow the stage and needle to move towards the cell while monitoring the potential and displacement of the stage to detect a fluctuation in voltage versus displacement to indicate that the needle has pierced the cell.

Embodiment 7

The method of any of the preceding Embodiments, wherein the calibration data comprises data defining voltages for displacements stored against types of cells.

Embodiment 8

The method of any of the preceding Embodiments, wherein the actuator is provided on an array of actuators, each interacting with an individual cell of a plurality of cells.

Embodiment 9

The method of any of Embodiments 4 to 8, wherein the cell trap comprises a plurality of microchambers, each microchamber arranged to hold a cell.

Embodiment 10

The method of any of Embodiments 6 to 9, wherein a laser interferometer is used to indicate that the needle has pierced the cell.

Embodiment 11

A method of generating calibration data for target voltage potentials associated with cell-type data, the method comprising:
  providing a calibration apparatus comprising a manipulator and a cell trap, the manipulator comprising a tower, a stage, and a needle, wherein the needle is mounted on the stage;
  identifying a cell type to be calibrated;
  applying a voltage so as to pull the stage towards the tower in a retracted position;
  moving the manipulator to within a defined range of the cell-trap configured to house a cell type;
  changing the voltage to allow the stage and mounted needle to be forced away from the tower and the retracted position while measuring the displacement of the stage;
  determining when the needle has reached a target region; and
  recording actuation data for use in cell injection for the identified cell type.

Embodiment 12

The method of Embodiment 11, further comprising receiving a user input of the cell type to a controller provided on the calibration apparatus.

Embodiment 13

The method of Embodiments 11 and 12, further comprising applying a voltage to an actuator provided on the calibration apparatus, so as to pull the stage towards the tower in a retracted position.

Embodiment 14

The method of Embodiments 11 to 13, further comprising moving the manipulator to within the defined range of the cell-trap, wherein a camera provided on the calibration apparatus is programmed to determine if the manipulator is within the defined range.

Embodiment 15

The method of Embodiment 14, wherein the camera on the calibration apparatus is programmed to determine if the manipulator is within the defined range of a periphery of the cell trap.

Embodiment 16

The method of Embodiments 11 to 15, further comprising reducing the voltage to allow the stage and mounted needle to be forced away from the tower and the retracted position while measuring the displacement of the stage.

Embodiment 17

The method of Embodiment 16, wherein measuring the displacement of the stage is performed by a laser interferometer provided in the calibration apparatus.

Embodiment 18

The method of Embodiments 11 to 17, wherein the actuation data is selected from a group consisting of a record target voltage, a target vertical actuation displacement, a point of penetration, a point of poking, a Voltage-Displacement characteristic curve distortion, and combinations thereof.

Embodiment 19

A non-transitory computer-readable medium in which a program is stored for causing a computer to perform a method for generating calibration data for target voltage potentials associated with cell-type data, the method comprising:
  providing a calibration apparatus comprising a manipulator and a cell trap, the manipulator comprising a tower, a stage, and a needle, wherein the needle is mounted on the stage;
  identifying a cell type to be calibrated;
  applying a voltage so as to pull the stage towards the tower in a retracted position;
  moving the manipulator to within a defined range of the cell-trap configured to house a cell type;
  changing the voltage to allow the stage and mounted needle to be forced away from the tower and the retracted position while measuring the displacement of the stage;
  determining when the needle has reached a target region; and
  recording actuation data for use in cell injection for the identified cell type.

Embodiment 20

The method of Embodiment 19, further comprising receiving a user input of the cell type to a controller provided on the calibration apparatus.

Embodiment 21

The method of Embodiments 19 and 20, further comprising applying a voltage to an actuator provided on the calibration apparatus, so as to pull the stage towards the tower in a retracted position.

Embodiment 22

The method of Embodiments 19 to 21, further comprising moving the manipulator to within the defined range of the cell-trap, wherein a camera provided on the calibration apparatus is programmed to determine if the manipulator is within the defined range.

Embodiment 23

The method of Embodiment 22, wherein the camera on the calibration apparatus is programmed to determine if the manipulator is within the defined range of a periphery of the cell trap.

Embodiment 24

The method of Embodiments 19 to 23, further comprising reducing the voltage to allow the stage and mounted needle to be forced away from the tower and the retracted position while measuring the displacement of the stage.

Embodiment 25

The method of Embodiment 24, wherein measuring the displacement of the stage is performed by a laser interferometer provided in the calibration apparatus.

Embodiment 26

The method of Embodiments 19 to 25, wherein the actuation data is selected from a group consisting of a record target voltage, a target vertical actuation displacement, a point of penetration, a point of poking, a Voltage-Displacement characteristic curve distortion, and combinations thereof.

Embodiment 27

A system for controlling a needle actuation to interact with a cell, the system comprising:
  an injection device comprising a tower, stage, needle and actuator, the needle mounted on the stage, and the actuator arranged and configured to apply a voltage potential to the stage to move the needle toward and away from the tower;
  a cell trap configured to house a cell to be penetrated by the needle of the injection device;
  a first camera configured and arranged to monitor a proximity of the injection device to the cell trap; and
  a controller configured to control the movement of the injection device.

Embodiment 28

The system of Embodiment 27, wherein the first camera is configured and arranged to monitor movement on a Z-axis.

Embodiment 29

The system of Embodiments 27 and 28, wherein the injection device further comprises a plurality of actuators.

Embodiment 30

The system of Embodiments 27 to 29, wherein the system further comprises a second camera configured and arranged to monitor the alignment between the injection device and the cell trap.

Embodiment 31

The system of Embodiment 30, wherein the first camera is configured and arranged to monitor movement on a Z-axis, and wherein the second camera is configured and arranged to monitor movement on the X-axis and Y-axis.

Embodiment 32

The system of Embodiments 27 to 29, wherein the system further comprises a microscope comprising a second camera, the microscope configured and arranged to monitor the alignment between the injection device and the cell trap.

Embodiment 33

The system of Embodiment 32, wherein the first camera is configured and arranged to monitor movement on a Z-axis, and wherein the microscope is configured and arranged to monitor movement on the X-axis and Y-axis.

Embodiment 34

The method of Embodiments 32 and 33, wherein the microscope is an inverted microscope.

Embodiment 35

The method of Embodiments 27 to 34, the system further comprising a macro-stage configured and arranged to control movement of the injection device.

Embodiment 36

A method for controlling a cell injection device, the method comprising:
  providing an apparatus comprising a cell injection device, a cell trap, and a storage device, the cell injection device comprising a tower, a stage, and a needle, wherein the needle is mounted on the stage;
  identifying a cell type to be injected;
  retrieving actuation data from the storage device;
  applying a voltage so as to pull the stage towards the tower in a retracted position;
  moving the cell injection device to within a defined range of the cell-trap configured to house a cell type;
  applying a varying target actuation voltage based on retrieved actuation data to allow the stage and mounted needle to be forced away from the tower and the retracted position;
  determining when the needle has reached a target region; and
  adjusting the voltage to move the needle towards the retracted position.

Embodiment 37

The method of Embodiment 36, further comprising receiving a user input of the cell type to a controller provided on the apparatus.

Embodiment 38

The method of Embodiments 36 and 37, further comprising applying a voltage to an actuator provided on the injection device, so as to pull the stage towards the tower in a retracted position.

Embodiment 39

The method of Embodiments 36 to 38, further comprising moving the injection device to within the defined range of the cell-trap, wherein a camera provided on the apparatus is programmed to determine if the injection device is within the defined range.

Embodiment 40

The method of Embodiment 39, wherein the camera on the apparatus is programmed to determine if the injection device is within the defined range of a periphery of the cell trap.

Embodiment 41

The method of Embodiments 36 to 40, wherein the actuation data is selected from a group consisting of a record target voltage, a target vertical actuation displacement, a point of penetration, a point of poking, a Voltage-Displacement characteristic curve distortion, and combinations thereof.

Embodiment 42

A non-transitory computer-readable medium in which a program is stored for causing a computer to perform a method for controlling a cell injection device, the method comprising:
  providing an apparatus comprising a cell injection device, a cell trap, and a storage device, the cell injection device comprising a tower, a stage, and a needle, wherein the needle is mounted on the stage;
  identifying a cell type to be injected;
  retrieving actuation data from the storage device;
  applying a voltage so as to pull the stage towards the tower in a retracted position;
  moving the cell injection device to within a defined range of the cell-trap configured to house a cell type;
  applying a varying target actuation voltage based on retrieved actuation data to allow the stage and mounted needle to be forced away from the tower and the retracted position;
  determining when the needle has reached a target region; and
  adjusting the voltage to move the needle towards the retracted position.

Embodiment 43

The method of Embodiment 42, further comprising receiving a user input of the cell type to a controller provided on the apparatus.

Embodiment 44

The method of Embodiments 42 and 43, further comprising applying a voltage to an actuator provided on the injection device, so as to pull the stage towards the tower in a retracted position.

Embodiment 45

The method of Embodiments 42 to 44, further comprising moving the injection device to within the defined range of the cell-trap, wherein a camera provided on the apparatus is programmed to determine if the injection device is within the defined range.

Embodiment 46

The method of Embodiment 45, wherein the camera on the apparatus is programmed to determine if the injection device is within the defined range of a periphery of the cell trap.

Embodiment 47

The method of Embodiments 42 to 47, wherein the actuation data is selected from a group consisting of a record target voltage, a target vertical actuation displacement, a point of penetration, a point of poking, a Voltage-Displacement characteristic curve distortion, and combinations thereof.

In the preceding description and the following claims the word "comprise" or equivalent variations thereof is used in an inclusive sense to specify the presence of the stated feature or features. This term does not preclude the presence or addition of further features in various embodiments.

It is to be understood that the present invention is not limited to the embodiments described herein and further and additional embodiments within the spirit and scope of the invention will be apparent to the skilled reader from the examples illustrated with reference to the drawings. In particular, the invention may reside in any combination of features described herein, or may reside in alternative embodiments or combinations of these features with known equivalents to given features. Modifications and variations of the example embodiments of the invention discussed above will be apparent to those skilled in the art and may be made without departure of the scope of the invention as defined in the appended claims.

What is claimed is:
1. A method of controlling a needle actuator to interact with an object or a cell, the method comprising:
  providing an actuator comprising a tower, a stage and a needle, wherein the needle is mounted perpendicularly on a planar surface of the stage, and the stage is suspended by a flexible tether;
  applying an electrostatic potential between the tower and the stage to pull the tower and the stage close to one another so as to retract the needle;
  moving the actuator towards the object or the cell;
  reducing the electrostatic potential so as to allow the tower and the stage to move apart from one another, thereby allowing the stage and needle to move towards the object or the cell;
  applying calibration data to detect when the needle has pierced the object or the cell; and
  reducing the electrostatic potential further once it has been detected that the needle has pierced the object or the cell.

2. The method of claim 1, wherein the cell is a biological cell.

3. The method of claim 1, wherein the needle is a micro-needle and the stage is a micro-stage.

4. The method of claim 1, wherein the cell is held by a cell trap.

5. The method of claim 1, further comprising applying the electrostatic potential between the tower and the stage to retract the needle towards the tower.

6. The method of claim 1, further comprising reducing the electrostatic potential to allow the stage and the needle to move towards the cell while monitoring the electrostatic potential and displacement of the stage to detect a fluctuation in voltage versus the displacement of the stage to indicate that the needle has pierced the object or the cell.

7. The method of claim 1, wherein the calibration data comprises data defining voltages for displacements for different types of cells based on a cell size or a membrane thickness.

8. The method of claim 1, wherein the actuator is provided on an array of actuators, each interacting with an individual cell of a plurality of cells.

9. The method of claim 4, wherein the cell trap comprises a plurality of microchambers, each microchamber arranged to hold a cell.

10. The method of claim 6, wherein a laser interferometer is used to indicate that the needle has pierced the cell.

11. A system for controlling a needle actuation to interact with a cell, the system comprising:
an injection device comprising a tower, stage, needle and actuator, the needle mounted on the stage, and the actuator arranged and configured to apply a voltage potential to the stage to move the needle toward and away from the tower;
a cell trap configured to house a cell to be penetrated by the needle of the injection device;
a first camera configured and arranged to monitor a proximity of the injection device to the cell trap; and
a controller configured to perform the method of claim 1.

12. A method for controlling an apparatus, the method comprising:
providing the apparatus comprising an actuator, a cell trap, and a storage device, the actuator comprising a tower, a stage, and a needle, wherein the needle is mounted vertically on the stage with a base of the needle attached normal to a flat surface of the stage, and the stage is suspended by a flexible tether;
retrieving actuation data from the storage device;
applying a voltage so as to pull the stage towards the tower in a retracted position;
moving the actuator to within a defined range of the cell trap configured to house a cell;
applying a varying target actuation voltage based on retrieved actuation data to allow the stage and mounted needle to be forced away from the tower and the retracted position;
determining when the needle has reached a target region; and
adjusting the voltage to move the needle towards the retracted position.

13. The method of claim 12, further comprising:
receiving a user input of the cell type to a controller provided on the apparatus.

14. The method of claim 12, wherein applying the voltage comprises applying a first voltage, the method further comprising:
applying a second voltage to the actuator so as to pull the stage towards the tower to the retracted position.

15. The method of claim 12, wherein while moving the actuator to within the defined range of the cell trap, a camera provided on the apparatus is programmed to determine if the actuator is within the defined range.

16. The method of claim 15, wherein the camera provided on the apparatus is programmed to determine if the actuator is within the defined range of a periphery of the cell trap.

17. The method of claim 12, wherein the actuation data is selected from a group consisting of a record target voltage, a target vertical actuation displacement, a point of penetration, a point of poking, a Voltage-Displacement characteristic curve distortion, and combinations thereof.

18. A non-transitory computer-readable medium in which a program is stored for causing a computer to perform a method for controlling an apparatus, the method comprising:
providing the apparatus comprising an actuator, a cell trap, and a storage device, the actuator comprising a tower, a stage, and a needle, wherein the needle is mounted normal to a planar surface of the stage, and the stage is suspended by a flexible tether;
retrieving actuation data from the storage device;
applying a voltage so as to pull the stage towards the tower in a retracted position;
moving the actuator to within a defined range of the cell trap configured to house a cell;
applying a varying target actuation voltage based on retrieved actuation data to allow the stage and mounted needle to be forced away from the tower and the retracted position;
determining when the needle has reached a target region; and
adjusting the voltage to move the needle towards the retracted position.

19. The non-transitory computer-readable medium of claim 18, further comprising:
receiving a user input of the cell to a controller provided on the apparatus.

20. The non-transitory computer-readable medium of claim 18, wherein applying the voltage comprises applying a first voltage, the method further comprising:
applying a second voltage to the actuator so as to pull the stage towards the tower to the retracted position.

21. The non-transitory computer-readable medium of claim 18, wherein while moving the actuator to within the defined range of the cell trap, a camera provided on the apparatus is programmed to determine if the actuator is within the defined range.

22. The non-transitory computer-readable medium of claim 21, wherein the camera provided on the apparatus is programmed to determine if the actuator is within the defined range of a periphery of the cell trap.

23. The non-transitory computer-readable medium of claim 18, wherein the actuation data is selected from a group consisting of a record target voltage, a target vertical actuation displacement, a point of penetration, a point of poking, a Voltage-Displacement characteristic curve distortion, and combinations thereof.

* * * * *